United States Patent
Josefowitz et al.

(10) Patent No.: US 10,350,188 B2
(45) Date of Patent: Jul. 16, 2019

(54) USE OF NEU1 SIALIDASE INHIBITORS IN THE TREATMENT OF CANCER

(75) Inventors: Paul Zachary Josefowitz, London (GB); Constantin Melas-Kyriazl, legal representative, Lausanne (CH); Myron R. Szewczuk, Kingston (CA)

(73) Assignee: Myron R. Szewczuk, Kingston, Ontario ( * ) Notice: Subject to any disclaimer, the term of this patent is extended or adjusted under 35 U.S.C. 154(b) by 800 days.

(21) Appl. No.: 14/370,916

(22) PCT Filed: Nov. 4, 2011

(86) PCT No.: PCT/CA2011/050690
§ 371 (c)(1),
(2), (4) Date: Feb. 5, 2015

(87) PCT Pub. No.: WO2013/063679
PCT Pub. Date: May 10, 2013

(65) Prior Publication Data
US 2015/0064282 A1 Mar. 5, 2015

(51) Int. Cl.
*A61K 31/215* (2006.01)
*A61K 31/505* (2006.01)
*A61K 31/135* (2006.01)
*A61K 31/70* (2006.01)
*A61K 31/00* (2006.01)
(Continued)

(52) U.S. Cl.
CPC .......... *A61K 31/215* (2013.01); *A61K 31/138* (2013.01); *A61K 31/196* (2013.01); *A61K 31/337* (2013.01); *A61K 31/351* (2013.01); *A61K 31/357* (2013.01); *A61K 31/513* (2013.01); *A61K 31/519* (2013.01); *A61K 31/7012* (2013.01); *A61K 31/7068* (2013.01); *A61K 33/24* (2013.01); *A61K 45/06* (2013.01); *C07C 233/23* (2013.01); *C07C 233/41* (2013.01); *C07D 309/30* (2013.01); *C07D 317/46* (2013.01); *C07D 317/68* (2013.01); *A61K 9/0019* (2013.01)

(58) Field of Classification Search
CPC .................................................... A61K 31/215
USPC ......................................................... 514/529
See application file for complete search history.

(56) References Cited

U.S. PATENT DOCUMENTS

| | | | |
|---|---|---|---|
| 5,792,842 A | 8/1998 | Iida | |
| 6,596,690 B2 * | 7/2003 | Tosato | C07K 14/4725 514/16.7 |

(Continued)

FOREIGN PATENT DOCUMENTS

| | | |
|---|---|---|
| CN | 101632659 A | 1/2010 |
| CN | 101910118 A | 12/2010 |

(Continued)

OTHER PUBLICATIONS

Amith, et al. Glycoconj J (2009) 26:1197-1212.*
(Continued)

*Primary Examiner* — Shengjun Wang
(74) *Attorney, Agent, or Firm* — RatnerPrestia

(57) ABSTRACT

Use of Neu1 sialidase inhibitors for the treatment of cancer as a monotherapy or in combination with known chemotherapeutics. Preferably, Neu1 sialidase inhibitors are oseltamivir phosphate or 2-deoxy-2,3-dehydro-N-acetylneuraminic acid (DANA) or analogs thereof.

16 Claims, 6 Drawing Sheets

(51) Int. Cl.

| | |
|---|---|
| *A61K 33/24* | (2019.01) |
| *C07D 309/30* | (2006.01) |
| *C07D 317/46* | (2006.01) |
| *A61K 45/06* | (2006.01) |
| *A61K 31/138* | (2006.01) |
| *A61K 31/337* | (2006.01) |
| *A61K 31/357* | (2006.01) |
| *A61K 31/513* | (2006.01) |
| *A61K 31/519* | (2006.01) |
| *A61K 31/7012* | (2006.01) |
| *A61K 31/7068* | (2006.01) |
| *A61K 31/196* | (2006.01) |
| *A61K 31/351* | (2006.01) |
| *C07C 233/23* | (2006.01) |
| *C07C 233/41* | (2006.01) |
| *C07D 317/68* | (2006.01) |
| *A61K 9/00* | (2006.01) |

(56) References Cited

U.S. PATENT DOCUMENTS

| | | | | |
|---|---|---|---|---|
| 7,390,782 | B2 * | 6/2008 | Newell | A61K 38/1825 |
| | | | | 514/18.9 |
| 7,494,671 | B2 * | 2/2009 | Wong | A61K 36/185 |
| | | | | 424/725 |
| 9,217,157 | B2 * | 12/2015 | Garcia-Sastre | C07K 14/005 |
| 9,295,682 | B2 * | 3/2016 | Nunes | A61K 31/661 |
| 9,789,202 | B2 * | 10/2017 | Jung | A61K 9/0019 |
| 9,795,672 | B2 * | 10/2017 | Fyfe | A61K 39/3955 |
| 2003/0077616 | A1 * | 4/2003 | Lomas | G01N 33/543 |
| | | | | 435/6.12 |
| 2005/0272688 | A1 | 12/2005 | Higgins | |
| 2006/0074047 | A1 | 4/2006 | Cross | |

FOREIGN PATENT DOCUMENTS

| | | | |
|---|---|---|---|
| EP | 0882721 | | 12/1999 |
| WO | WO 2006/082435 A1 * | | 8/2006 |
| WO | WO 2009/087062 A2 | | 7/2009 |
| WO | 2009137916 | | 11/2009 |
| WO | WO 2009/137916 A1 * | | 11/2009 |
| WO | 2011047466 | | 4/2011 |
| WO | 2012006550 | | 1/2012 |

OTHER PUBLICATIONS

Abrecht et al., Chimia 58 (2004) 621-629.*
Miyagi et al., J. Biochem. 144, 279-285 (2008).*
Hayden, et al., JAMA. 1999;282(13):1240-1246. doi:10.1001/jama.282.13.1240.*
Ramkumar et al., Molecules 2010, 15, 3958-3992.*
Ko, Andrew, Andrews McMeel Publishing, Jan. 1, 2009, Health & Fitness, 1024 pages, Revised 5$^{th}$ Edition, Everyone's Guide to Cancer Therapy: How Cancer Is Diagnosed, Treated, and Managed Day to Day.*
Chabner et. al, Nature Reviews Cancer, 2005, Nature Publishing Group, vol. 5, pp. 65-72.*
Leaf, Fortune, Mar. 9, 2004, Time Inc., pp. 1-28.*
Hata et al. "limited inhibitory effect of oseltamivir and zanamivir on human sialidases," Antimicribial agents and Chemotherapy, 2008 , vol. 52, No. 10, pp. 3484-3491, (Year: 2008).*
Tamiflu, Wikipedia, 2018 (Year: 2018).*
"Tamiflu" Genentach, Inc. 2008 (available at https://www.fda.gov/downloads/Drugs/DrugSafety/InformationbyDrugClass/ucm147992.pdf ) (Year: 2008).*
Abdulkhalek et al., Journal ofBiological Chemistry (2011), 286(42): 36532-36549.
Amith et al., Cell Signal 2010, 22, 314-324.
Amith et al., Glycoconj Journal 2009, 26, 1197-1212.
Arabkhari et al., Glycobiology 2010, 20(5), 603-616.
Chen et al., J Immunol 1997, 158, 3070-3080.
Hata et al., Antimicrob Agents Chemother 2008, 52(10), 3484-3491.
Hinek et al., J.Biol.Chem. 2006, 281(6), 3698-3710.
Hu et al., Nature Reviews, Drug Discovery 2007, vol. 6, 480-498.
International Preliminary Report on Patentability for International Application No. PCT/CA2011/050690 dated May 6, 2014.
International Search Report for International Application No. PCT/CA2011/050690 dated Jul. 11, 2012.
Jayanth et al., Cell Signal 2010, 22, 1193-1205.
Li et al., J Clin Invest 2007, 117(2), 346-352.
Liu et al., Oncol Rep 2007, 18, 673-677.
Lukong et al., Hum.Mol.Genet. 2000, 9(7), 1075-1085.
Magesh et al., Biorganic and Medicinal Chemistry Letters 2008, (18), 532-537.vbTab.
Miyagi et al., J.Biochem.(Tokyo) 1990, 107, 794-798.
Morimoto et al., Drug Metab Dispos 2008, 36(1), 6-9.
Nan et al., J Leukoc Biol 2007, 81, 284-296.
Papini et al., J.Biol.Chem. 2004, 279(17), 16989-16995.
Rodriguez et al., J.Neurosci. 2001, 21(21), 8387-8395.
Sasaki et al., J.Biol.Chem. 2003, 278(30), 27896-27902.
Seyrantepe et al., Hum.Mutat. 2003, 22, 343-352.
Seyrantepe et al., Journal of Biological Chemistry 2010, 285(1), 206-215.
Shi et al., J Pharmacol Exp Ther 2006, 319(3), 1477-1484.
Takahashi et al., Biochim Biophys Acta 2008, 1780, 520-524.
Takahashi et al., Glycoconj Journal 2004, 20, 207-212.
Uberall et al., Exp Mol Pathol 2008, 84, 79-89.
Uemura et al., Oncogene (2009), 28: 1218-1229.
Woronowicz et al., Glycobiology 2006, 17(1), 10-24.
Yamaguchi et al., Biochem.J. 2005, 390, 85-93.
Yogalingam et al., Dev Cell 2008, 15(1), 74-86.
Zwick et al., Trends Mol Med 2002, 8(1), 17-23.
Xu et al., Basic & Clinical Medicine, 30(2):139-43 (2010). (Abstract).
Abdulkhalek et al. "Neu 1 Sialidase and matrix Metalloproteinase-9 Cross-Talk: a Novel Molecular Signalling Platform for Cell Surface and Intracellular TOLL-Like Receptors"—2010 Annual Conference of the Society for Glycobiology, Nov. 7-10, 2010, St. Petersburg Beach, FL. (Abstract).
Ademidun et al. "Inhibitory Potency of Tamiflu and DANA and their Modified Derivative on Lipopolysaccharide-Induced Neu1 Sialidase Activity in Live BMA Macrophage Cells"—2010 Annual Conference of the Society for Glycobiology, Nov. 7-10, 2010, St. Petersburg Beach, FL. (Abstract).
Gilmour et al., Ligand-Induced EGFR Activation is dependent on Neu1 Sialidase and MMP-9 Cross-Talk poster presentation—2010 Annual Conference of the Society for Glycobiology, Nov. 7-10, 2010, St. Petersburg Beach, FL. (Abstract).
Bruns et al., Clinical Cancer Research, vol. 6, May 2000, pp. 1936-1948.
European Search Report for European Application No. EP 11 87 4886 completed Mar. 12, 2015.
Gilmour et al., "The Role of NEU1 Sialidase in Epidermal Growth Factor Receptor Activation," Jun. 1, 2011, pp. 1-103.
Govorkova et al., Viruses, vol. 2, No. 8, Jul. 27, 2010, pp. 1510-1529.
Saif, Anticancer Research, vol. 31, Mar. 1, 2011, pp. 1039-1042.
Solórzano et al., Clinical Cancer Research, vol. 7, No. 8, Aug. 1, 2001, pp. 2563-2572.
Thacker et al., "Meera Thacker Rob Shulman Mike Kidd United Clinical Pharmacy Association Kingdom Antiviral management of Influenza A (H1N1) in Critical Care Contents," Jan. 1, 2011, Version 4.0, pp. 1-29.
Yu et al., Chinese Journal of Pathophysiology, 25(3):502-04 (2009).

* cited by examiner

Prior Art

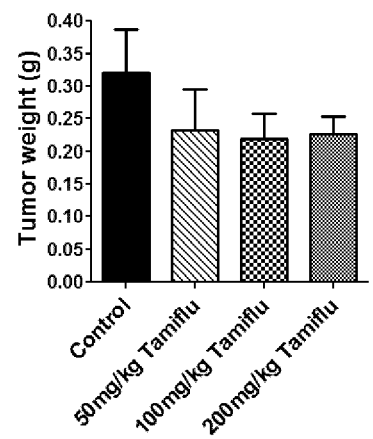
Figure 3a
Untreated Day 47        Tamiflu
                        (100 mg/kg) D47
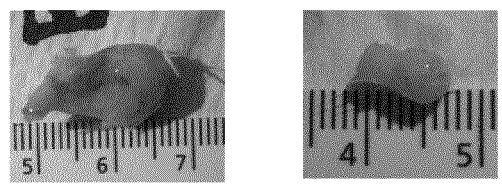
Figure 3b
MiaPaCa-eGFP      Untreated D 47      Tamiflu
(Fluorescence)    (Biophotonics)      (Biophotonics)
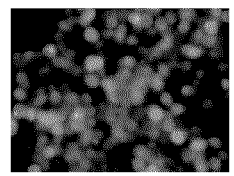 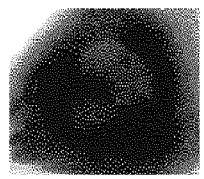 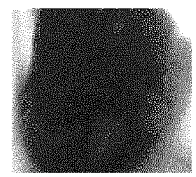
 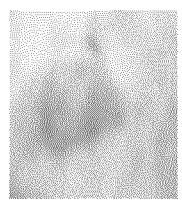
Figure 3c

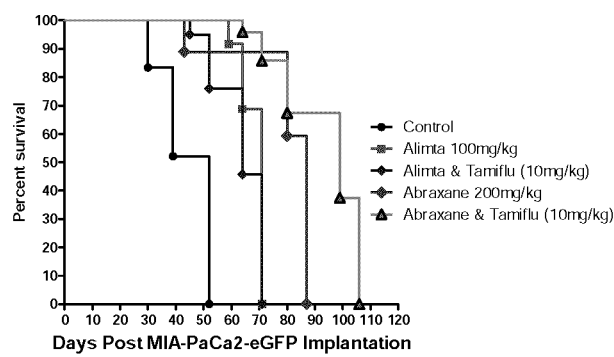 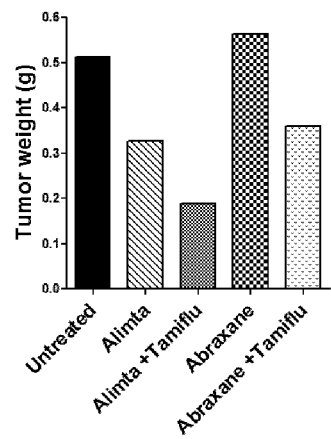
Figure 4a                                   Figure 4b

USE OF NEU1 SIALIDASE INHIBITORS IN THE TREATMENT OF CANCER

FIELD OF THE INVENTION

The present invention relates to the field of cancer treatment and in particular to the use of oseltamivir and analogues thereof for the treatment of cancer and in particular pancreatic cancer.

BACKGROUND OF THE INVENTION

Oseltamivir Phosphate

Oseltamivir phosphate (sold by Hoffman la Roche under the trade name Tamiflu) is the prodrug form of the known viral neuraminidase inhibitor oseltamivir carboxylate, which is used in the treatment and prophylaxis of influenza and other similar viruses. Oseltamivir phosphate is itself not effective as an antiviral; it is the ethyl ester prodrug of the active antiviral agent oseltamivir carboxylate. The oseltamivir phosphate which is administered orally for use as an antiviral, is metabolized in the liver by the carboxyesterase enzyme to the active anti-viral form. Oseltamivir is a competitive inhibitor of sialic acid found on the surface proteins of normal host cells. The antiviral agent works by blocking the activity of the viral neuraminidase enzyme, preventing new viral particles from being released by infected cells.

Methods of preparing oseltamivir and derivatives or analogues thereof, have been described in the patent literature, for example, in PCT publications WO 2009/137916 (hereinafter '916) to Hudlicky et al. [1] and WO 2011/047466 (hereinafter '466) to Hudlicky et al. [2]], incorporated herein by reference. The '916 and '466 patent publications further describe intermediates useful for the process for preparing oseltamivir and derivatives thereof.

Cancer Treatment

Worldwide, millions of people die from cancer every year. The American cancer society reports that half of all men and one-third of all women in the United States will develop cancer during their lifetimes. Today millions of people are living with cancer or have had cancer. The US National Cancer Institute's Surveillance Epidemiology and End Results (SEER) study estimated cancer prevalence, in the United States in 2007 at 11,714,000.

Carcinomas of the lung, prostate, breast, colon, pancreas, and ovary have a high incidence of cancer death especially if the cancer is found at a late stage of progression. These and virtually all other carcinomas may further lead to metastatic disease which in many instances is fatal. Moreover, even for those cancer patients who initially survive their primary cancers, there is still a risk of recurrence.

In particular, patients with pancreatic cancer often present with advanced disease that is lethal and difficult to treat. Despite routine use of chemotherapy and radiotherapy, survival rate of patients with advanced pancreatic cancer has not improved dramatically. Chemo- and radiotherapy provide little or no benefit. These outcomes demand an urgent need for novel therapeutic approaches. Consequently, the development of novel cancer treatment strategies is critically essential to improve the clinical management and prognosis of cancer patients and in particular patients with pancreatic cancer.

Research in the field of cancer treatment has looked at ways to modulate cellular pathways that are essential for cancer to survive and grow. Numerous receptors and molecular pathways have been implicated in oncogenesis and cancer growth and proliferation including Ras, EGFR, VEGF, gastrin and matrix metalloproteinases.

The epidermal growth factor receptor (EGFR; ErbB-1; HER1 in humans) is the cell surface receptor member of the epidermal growth factor (EGF-family) of extracellular protein ligands. The EGFR is a member of the ErbB family of receptors, a subfamily of four closely related receptor tyrosine kinases: EGFR (ErbB-1), HER2/c-neu (ErbB-2), Her 3 (ErbB-3) and HER 4 (ErbB-4). Mutations affecting EGFR expression or activity could result in cancer.

The Ras subfamily (an abbreviation of RAt Sarcoma) is a protein subfamily of small GTPases that are involved in cellular signal transduction. Activation of Ras signaling causes cell growth, differentiation and survival.

All members of the vascular endothelial growth factor (VEGF) family stimulate cellular responses by binding to tyrosine kinase receptors (the VEGFRs) on the cell surface, causing them to dimerize and become activated through autophosphorylation. VEGF is a signal protein produced by cells that stimulates vasculogenesis and angiogenesis.

In humans, gastrin is a hormone that stimulates secretion of gastric acid (HCl) by the parietal cells of the stomach and aids in gastric motility. It is released by G cells in the stomach, duodenum, and the pancreas. Its release is stimulated by peptides in the lumen of the stomach.

Matrix metalloproteinases (MMPs) are zinc-dependent endopeptidases as well as adamalysins, serralysins, and astacins. The MMPs belong to a larger family of proteases known as the metzincin superfamily. They are capable of degrading all kinds of extracellular matrix proteins, but also can process a number of bioactive molecules. They are also known to be involved in the cleavage of cell surface receptors, the release of apoptotic ligands (such as the FAS ligand), and chemokine/cytokine inactivation [3].

Although the signalling pathways of many glycosylated receptors including EGFR, VEGF, insulin and others that have been implicated in cancer are well characterized, the parameters controlling interactions between these receptors and their ligands have remained poorly defined. A novel signalling paradigm of glycosylated receptor activation by their natural ligands has been identified [4-7].

Toll-Like Receptor (TLR)

It has been discloses that ligand-induced TOLL-like receptor (TLR) activation is controlled by Neu1 sialidase activation. Studies have shown that Neu1 is already in complex with the TOLL-like receptors, and activation is induced upon ligand binding of the natural ligands to their respective receptors. In addition, activated Neu1 specifically hydrolyzes α-2,3-sialyl residues linked to β-galactoside, which are distant from the ligand binding site. This removes steric hindrance to receptor dimerization, and leads to subsequent signalling pathways [4,6].

It has been found that the neuraminidase inhibitor, oseltamivir phosphate, specifically inhibits TLR ligand-induced Neu1 activity on the cell surface of macrophage and dendritic cells, and subsequently blocks TLR ligand induced NFkB activation, nitric oxide (NO) production and pro-inflammatory cytokines [4]. In addition, other purified neuraminidase inhibitors such as BCX-1827, DANA (2-deoxy-2,3-dehydro-N-acetylneuraminic acid), zanamivir (4-guanidino-Neu5Ac2en), and oseltamivir carboxylate had a limited effect on inhibition of lypopolysaccharide (LPS) induced sialidase activity in live BMC-2 macrophage cells at 1-2 mM compared to the LPS positive control.

Other studies using recombinant soluble human sialidases have shown that oseltamivir carboxylate scarcely inhibited the activities of the four human sialidases even at 1 mM [8], while zanamivir significantly inhibited the human Neu2 and Neu3 sialidases in the micromolar range. Furthermore, Nan et al. using lysates from mature dendritic cells have found that zanamivir completely inhibited Neu1 and Neu3 sialidase activity at 2 mM [9].

Interesting it has been found that oseltamivir phosphate was the most potent compared to the other neuraminidase inhibitors in inhibiting the sialidase activity associated with TLR ligand treated live macrophage cells whereas this compound is known to be ineffective as an antiviral in vitro because its antiviral activity is achieved by its hydrolytic metabolite oseltamivir carboxylate [10].

To further elucidate the inhibitory capacity of oseltamivir phosphate and its hydrolytic metabolite oseltamivir carboxylate, the 50% inhibitory concentration (IC50) of each compound was determined by plotting the decrease in sialidase activity against the log of the agent concentration. It was shown that oseltamivir phosphate had an IC50 of 1.175 µM compared to an IC50 of 1015 µM for oseltamivir carboxylate [4]. These data clearly illustrate that oseltamivir phosphate is 1000-fold more potent than its hydrolytic metabolite in inhibiting the sialidase activity associated with TLR ligand treated live BMC-2 macrophage cells.

It is possible that oseltamivir phosphate could be transported through the cell membrane by a P-glycoprotein as described by Morimoto et al. [11], where the hydrolytic activation could be catalyzed by carboxylesterase [10]. The antiplatelet agent clopidogrel has been previously determined to inhibit the hydrolysis of oseltamivir phosphate by carboxylesterase as much as 90% [10]. To determine whether the oseltamivir phosphate is hydrolysed in the cell in this live cell assay system, live BMA macrophage cells were pre-treated with clopidogrel bisulfate at 280 µM and 500 µM for 2 min followed with 5 µg/mL of endotoxin lipopolysaccharide (LPS) in the presence or absence of 400 µM pure oseltamivir phosphate. The results indicated that the anticarboxylesterase agent clopidogrel had no effect on oseltamivir phosphate's capacity to inhibit LPS induced sialidase activity [4]. Together, these results suggest that oseltamivir phosphate is a potent inhibitor of the sialidase associated with TLR ligand treated live macrophage cells.

Tyrosine Kinase (Trk) Receptor

The role of Neu1 sialidase as an intermediate link in the initial process of ligand induced tyrosine kinase (Trk) receptor activation and subsequent cellular function has been studied [12]. It is reported that Neu1 forms a complex with glycosylated Trk receptors within the ectodomain [12], which is consistent with the previous reported results with TLR receptors [13,14].

It has been shown Neu1 is a requisite intermediate in regulating Trk activation following neurotrophin binding to the receptor. Furthermore, based on previous findings, it is predicted that Neu1, activated by neurotrophin binding to the receptor, will result in a rapid removal of α-2,3-sialyl residues linked to β-galactosides on Trk ectodomain to generate a functional Trk receptor [12]. Although there are four identified mammalian sialidases classified according to their subcellular localization [15], the sialidases classified as cytosolic (Neu2), plasma membrane bound (Neu3) [16-18] and Neu4 [19,20] are not involved in the sialidase activity associated with neurotrophin treated live Trk-expressing cells and primary cortical neurons. Additionally, the potentiation of GPCR-signaling via membrane targeting of Gαi subunit proteins and matrix metalloproteinase-9 activation by ligand binding to the receptor is involved in the activation process of Neu1 sialidase on the cell surface [12].

Oseltamivir phosphate was found to be highly potent ($IC_{50}$ 3.876 µM) in inhibiting Neu1 activity induced by NGF treatment of live TrkA-expressing cells. The other neuraminidase inhibitors oseltamivir carboxylate and zanamivir had limited inhibitory effect on Neu1 sialidase activity associated with NGF treated live TrkA-expressing cells. It is speculated that the reason for the inhibitory potency of oseltamivir phosphate on Neu1 sialidase activity may be due to a unique orientation of Neu1 with the molecular multi-enzymatic complex that contains β-galactosidase and cathepsin A [21] and elastin-binding protein (EBP) [22], the complex of which would be associated within the ectodomain of Trk receptors. Another possibility may involve oseltamivir phosphate's direct effect on Neu1 sialidase with specificity for sialyl α-2,3 residues linked β-galactosyl linkage of TLR receptors. It has been reported that Neu1 desialylation of α-2,3-sialyl residues of TLR receptors enables receptor dimerization [14]. The data indicated that TLR ligand-induced NFκB responses were not observed in TLR deficient HEK293 cells, but were re-established in HEK293 cells stably transfected with TLR4/MD2, and were significantly inhibited by α-2,3-sialyl specific *Maackia amurensis* (MAL-2) lectin, α-2,3-sialyl specific galectin-1 and neuraminidase inhibitor oseltamivir phosphate but not by α-2,6-sialyl specific *Sambucus nigra* lectin (SNA).

Collectively, these findings suggest that Neu1 sialidase is one of the key regulators of neurotrophin-induced Trk activation to generate a functional receptor. Targeting Neu1 would be expected to be a key signalling inhibitor by blocking the NGF activation of the TrkA signal transduction pathway at the receptor level on the cell surface.

In other studies TrkA expression and kinase activity in human pancreatic cell lines PANC-1, MIA-PaCa-2 and APC-1 were shown to be directly correlated with gemcitabine chemo-resistance. It has been further shown that silencing RNA interference (siRNA) suppressed TrkA expression and kinase activity and furthermore increased gemcitabine induced, caspase-mediated apoptosis [23].

In other studies, Neu1 was found to negatively regulate lysosomal exocytosis in hematopoietic cells where it processes the sialic acids on the lysosomal membrane protein LAMP-1 [24]. On the cell surface, Seyrantepe et al. have shown that Neu1 can actually activate phagocytosis in macrophages and dendritic cells through the desialylation of surface receptors, including Fc receptors for immunoglobulin G (FcγR) [25]. Stomatos and colleagues have also shown that Neu1 on the cell surface is tightly associated with a subunit of cathepsin A and the resulting complex influences cell surface sialic acid in activated cells and the production of IFNγ [9]. Using Neu1-deficient mice, they produced markedly less IgE and IgG1 antibodies following immunization with protein antigens, which may be the result of their failure to produce IL-4 cytokine [26].

Understanding the ligand-induced EGFR activation has tremendous relevance in the fields of cancer biology and therapeutics. EGFR over-expression is often implicated in oncogenesis, where the downstream anti-apoptotic and pro-growth effects of EGFR signalling act to further reinforce a cancerous cell's strategies to survive and multiply. As such, analysis of EGFR expression and signalling is often incorporated into the clinical management of oncogenesis. For an example, EGFR over-expression is routinely used as a biomarker in the analysis of basal-like breast tumours, where it acts as a predictor of poor prognosis and a high rate of relapse and metastasis [27].

Additionally, the presence of EGFR mutants on a cell's surface can also have severe and negative effects on the cancer cell's survival. One of the major EGFR mutants implicated in an array of tumours is the EGFRvIII mutant, which contains a 267 amino acid deletion in the extracellular domain of the receptor, including 4 N-glycosylation sites [5, 28, 29]. The issues with this receptor stem from the fact that it remains constitutively active at all times, sending a continuous stream of pro-growth and division signals for the cancerous cell.

Novel cancer therapeutics have built upon this knowledge and function to inhibit the EGFR with the hope of shutting down its aberrant signalling pathways. There are two major forms of therapeutics which target the EGFR activation mechanism: the first involves the administration of high-affinity antibodies (ie. cetuximab) to competitively bind to the ligand-binding site, thus preventing ligand binding, and the second involves the administration of small-molecule inhibitors (ie. erlotinib, gefinitib) which bind to the tyrosine kinase portion of the receptor and inhibit its phosphorylation activity [30].

The PANC-1 cell line, a human carcinoma cell line derived from the pancreatic ductal epithelium, was used in an experiment to determine whether Neu1 sialidase was also playing a role in EGFR activation within a human pancreatic cancer model. The same results in this PANC-1 cell line were observed as were observed previously in the 3T3-hEGFR mouse fibroblast cell line in which EGF-stimulation of the EGFR rapidly induces Neu1 sialidase activity. Therefore, it is propose that Neu1 sialidase is essential for the ligand-induced EGFR activation mechanism and inhibition of Neu1 sialidase will inhibit EGFR [32].

SUMMARY OF THE INVENTION

It has been found that oseltamivir phosphate is an inhibitor of Neu1 sialidase and it has further been found that Neu1 sialidase acts through a receptor level signalling pathway, on the cell surface to modulate a number of other receptors. EGFR and Trk A are among the receptors found to be modulated by Neu1 sialidase; these receptors are known to play a role in cancer.

It has been found that oseltamivir phosphate is an effective anticancer agent in in vitro and in vivo studies. Oseltamivir phosphate has been shown to be an active anti-cancer agent against a variety of cancer cell types in vitro.

It has further been found that oseltamivir phosphate in combination with chemotherapeutic agents can improve the efficacy of the chemotherapeutic agent and can improve anti-cancer activity in cells that are refractory to standard chemotherapeutic treatment.

The present invention therefore includes a method of treating cancer comprising administering an effective amount of oseltamivir phosphate to a subject in need thereof.

The present invention also relates to a use of oseltamivir phosphate to treat cancer. Further, the present invention relates to a use of oseltamivir phosphate to prepare a medicament to treat cancer.

The present invention also includes a method of treating cancer comprising: administering to a subject in need thereof an therapeutically effective amount of
(a) oseltamivir phosphate; and
(b) one or more chemotherapeutic agents;
wherein (a) and (b) are performed concurrently or sequentially in any order.

The present invention further relates to a use of oseltamivir and one or more chemotherapeutic agents to treat cancer. Further, the present invention relates to a use of oseltamivir phosphate to prepare a medicament to treat cancer.

The present invention further relates to a method of preventing, inhibiting or reducing metastasis of a cancer comprising administering to a subject in need thereof oseltamivir phosphate either alone or in combination with a chemotherapeutic agent.

The present invention further relates to a use oseltamivir phosphate to prevent, inhibit or reduce metastasis of a cancer. Further the present invention relates to a use of oseltamivir phosphate in the preparation of a medicament for the prevention, inhibition or reduction of metastasis of a cancer.

It has been found that analogues of oseltamivir phosphate may act as inhibitors of Neu1 sialidase. It has also been found that such analogues act as anti-cancer agents against cancer cells in vitro.

The present invention further relates to a method of treating cancer comprising administering to a subject in need thereof a Neu1 sialidase inhibitor. The present invention further relates to a use of a Neu1 sialidase inhibitor to treat cancer. Further the present invention relates to a use of a Neu1 sialidase inhibitor in the preparation of a medicament for the treatment of cancer.

In a particular aspect of the invention the Neu1 sialidase inhibitor is oseltamivir phosphate or an analogue thereof.

In a further aspect of invention the Neu1 sialidase inhibitor may be administered as a monotherapy or as a co-treatment with a chemotherapeutic agent.

In an aspect of the invention the analogue of oseltamivir is a derivative of osletamivir phosphate or an intermediate, useful in the preparation of oseltamivir phosphate.

In an aspect of the invention the analogue is selected from a compound according to any one of formulas A-F:

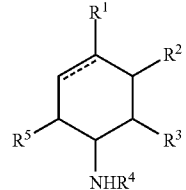

Formula A wherein,
$R^1$ is halo or $COOR^6$;
$R^2$ is OH or $OR^7$;
$R^3$ is OH, $OR^8$ or $N_3$;
$R^4$ is H or $C_{1-6}$acyl;
$R^5$ is $OC_{1-6}$alkyl, $SC_{1-6}$alkyl, OH, SH, halo, $N_3$, $NH_2$, $NHC_{1-6}$alkyl or $NHPG^4$ or
$R^4$ and $R^5$ are linked, together with the atoms to which they are attached, to form an oxazoline ring;
$R^6$ is $C_{1-6}$alkyl;
$R^7$ and $R^8$ are the same or different and are independently $C_{1-6}$alky, $C_{1-6}$ acyl or $PG^5$, or $R^7$ and $R^8$ are joined together with the oxygen atoms to which they are attached, to form a 5-membered cyclic ketal that is substituted on the carbon between the oxygen atoms by one or two $C_{1-6}$alkyl (preferably dimethy or diethyl ketal);
$PG^4$ and $PG^5$ are independently protecting groups.
----- represents a single or double bond and
one or more hydrogens in the $C_{1-6}$alkyl and/or $C_{1-6}$acyl groups is/are optionally replaced with F;

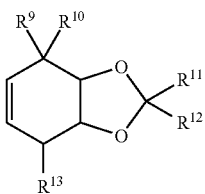

Formula B wherein
$R^9$ is $COOR^{14}$
$R^{10}$ is H, OH or $OC_{1-6}$acyl;
$R^{13}$ is $NHC_{1-6}$acyl;
or the O in $R^{10}$ and the N in $R^{13}$ are joined by a covalent bond;
$R^{11}$ and $R^{12}$ are independently $C_{1-6}$alkyl;
$R^{14}$ is $C_{1-6}$alkyl, and
one or more of the hydrogen atoms in the $C_{1-6}$alkyl and/or $C_{1-6}$acyl groups is/are optionally replaced with F;

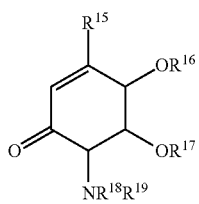

Formula C wherein,
$R^{15}$ is COOEt, COOMe, COOiPr, COOnPr, $COOCH_2C\equiv CH$, C(O)H, C(O)OH, $C(O)O^-$, $CCl_3$, CN, $C\equiv CH$, $CH_2C\equiv CH$ or $CH_2OH$;
$R^{16}$ and $R^{17}$ are independently H, $C_{1-6}$alky, $C_{1-6}$acyl or a suitable protecting group, or $R^{16}$ and $R^{17}$ are joined to form a suitable protecting group such as, a cyclic ketal that is optionally substituted on the carbon between the oxygen atoms by one or two $C_{1-6}$alkyl groups; and
$R^{18}$ and $R^{19}$ are independently H, $C_{1-6}$alky, $C_{1-6}$acyl or a suitable protecting group or $R^{18}$ and $R^{19}$ are joined to form a suitable protecting group;
wherein one or more hydrogens in $R^{15}$, $R^{16}$, $R^{17}$ $R_{18}$ and/or $R_{19}$ is are optionally replaced with F;

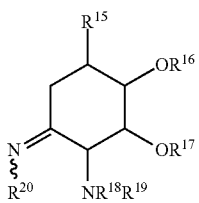

Formula D wherein,
$R^{15}$ is COOEt, COOMe, COOiPr. COOnPr, $COOCH_2C\equiv CH$, C(O)H, C(O)OH, $C(O)O^-$, $CCl_3$, CN, $C\equiv CH$, $CH_2C\equiv CH$ or $CH_2OH$;
$R^{16}$ and $R^{17}$ are independently H, $C_{1-6}$alky, $C_{1-6}$acyl or a suitable protecting group, or $R^{16}$ and $R^{17}$ are joined to form a suitable protecting group such as, a cyclic ketal that is optionally substituted on the carbon between the oxygen atoms by one or two $C_{1-6}$alkyl groups;

$R^{18}$ and $R^{19}$ are independently H, $C_{1-6}$alky, $C_{1-6}$acyl or a suitable protecting group or $R^{18}$ and $R^{19}$ are joined to form a suitable protecting group; and
$R^{20}$ is a group that is removed under reduction or hydrogenation reaction conditions or $R^{20}$ is a suitable acid labile protecting group, for example $R^{20}$ is OH, R, O—R, O(C)—R. $Si(R)_3$, $NO_2$, $NH_2$, $N(R)_2$, $S(O)_2R$ or $S(O)_2OR$, wherein each R is independently alkyl, aryl or heteroaryl and various substituted derivatives thereof.
wherein one or more hydrogens in $R^{15}$, $R^{16}$, $R^{17}$ $R^{18}$, $R^{19}$ and/or $R^{20}$ is/are optionally replaced with F;

Formula E

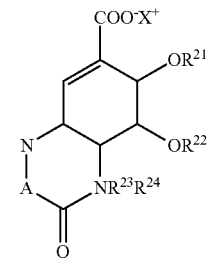

wherein,
X+ is a cation;
$R^{21}$ and $R^{22}$ are independently H, $C_{1-6}$alkyl or $C_{1-6}$acyl, or $R^{21}$ and $R^{22}$ are joined together with the atoms to which they are attached, to form a 5-10-membered ring that is unsubstituted or substituted with one or more halo or $C_{1-6}$alkyl;
$R^{23}$ and $R^{24}$ are independently H, $C_{1-6}$alkyl and $C_{1-6}$acyl;
$R^{25}$ is $OR^{26}$, $NR^{27}R^{28}$, =O or =$NR^{29}$;
$R^{26}$ is H, $C_{1-6}$alkyl or $C_{1-6}$acyl;
$R^{27}$ and $R^{28}$ are independently H, $C_{1-6}$alkyl or $C_{1-6}$acyl;
$R^{29}$ is H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}$alkyl$)(C_{1-6}$acyl or $NHC_{1-6}$acyl, or $R^{29}$ and one of $R^{23}$ and $R^{24}$ form a linker group "-A-C(O)—" to provide a compound of the formula:

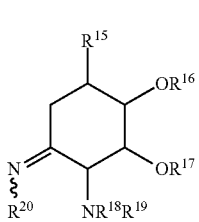

wherein A is O or NH; and
one or more available hydrogens in $R^{21}$, $R^{22}$, $R^{23}$, $R^{24}$, $R^{25}$, $R^{26}$, $R^{27}$, $R^{28}$ and/or $R^{29}$ is/are optionally replaced with F; or Formula F

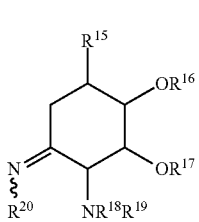

wherein,
X+ is a cation $R^{30}$ is H, $C_{1-6}$alkyl or $C_{1-6}$acyl;
$R^{31}$ and $R^{32}$ are independently F, $C_{1-6}$alkyl or $C_{1-6}$acyl or $R^{31}$ and $R^{32}$ are joined together, with the atoms to which they are attached, to form a 5-10-membered ring that is unsubstituted or substituted with one or more of halo or $C_{1-4}$alkyl;
$R^{33}$ and $R^{34}$ are independently H, $C_{1-6}$alkyl or $C_{1-6}$acyl; and one or more available hydrogen atoms in $R^{30}$, $R^{31}$, $R^{32}$, $R^{33}$ and/or $R^{34}$ is/are optionally replaced with F
or salts, solvates, prodrugs, stereoisomers or isotope-labelled forms thereof or mixtures thereof.

In a further aspect of the invention the analogue of oseltamivir phosphate is selected from a compound of the formula:

Sodium; 4-acetylamino-2-ethoxy-3,5-dihydroxy-cyclohexanecarboxylate (A1);

Sodium; 4-acetylamino-5-amino-3-hydroxy-cyclohex-1-enecarboxylate (A2);

Sodium; 7-acetylamino-4-hydroxy-2,2-dimethyl-3a,4,7,7a-tetrahydro-benzo[1,3]dioxole-4-carboxylate (A3);

Sodium; 7-acetylamino-6-hydroxy-2,2-dimethyl-3a,4,7,7a-tetrahydro-benzo[1,3]dioxole-4-carboxylate (A4);

Sodium; 7-acetylamino-6-hydroxyimino-2,2-dimethyl-3a,6,7,7a-tetrahydro-benzo[1,3]dioxole-4-carboxylate (A5) or Sodium; 7-acetylamino-6-(1-ethyl-propoxy)-2,2-dimethyl-3a,6,7,7a-tetrahydro-benzo[1,3]dioxole-4-carboxylate (A6).

In a further aspect the present invention includes a pharmaceutical composition comprising oseltamivir phosphate in a formulation that is suitable for injection. The present invention further includes pharmaceutical compositions comprising oseltamivir phosphate and one or more chemotherapeutic agents.

In a further aspect of the present invention includes a pharmaceutical composition comprising one or more analogues of oseltamivir phosphate and a pharmaceutically acceptable carrier. The present invention further includes pharmaceutical compositions comprising one or more analogues of oseltamivir phosphate and one or more chemotherapeutic agents.

In still a further aspect of the invention there is provided a kit comprising oseltamivir phosphate and instructions for use in the treatment of cancer. In still a further aspect of the invention there is provided a kit comprising oseltamivir phosphate and one or more chemotherapeutic agents and instructions for use.

In still a further aspect of the invention there is provided a kit comprising an analogue of oseltamivir phosphate and instruction for use in the treatment of cancer. In still another aspect of the invention, the kit further comprises one or more chemotherapeutic agents.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 3a shows tumour weights derived from RAG2/Cγ double mutant mice at day 48 post implantation with MiaPaCa-2-eGFP pancreatic cancer cells following intraperitoneal treatment with different dosages of soluble oseltamivir phosphate.

FIG. 3b shows tumour images at Day 46 from RAG2/Cγ double mutant mice implanted with MiaPaCa-2-eGFP pancreatic cancer cells following intraperitoneal treatment with soluble oseltamivir phosphate.

FIG. 3c shows fluorescent images of cells before implantation using Zeiss M2 fluorescence microscope.

FIG. 4a shows survival rates of RAG2/Cγ double mutant mice implanted with MiaPaCa-2-eGFP pancreatic cancer cells following intraperitoneal co-treatment with soluble oseltamivir phosphate daily and Alimta or Abraxane once. Survival curves are significantly different (p<0.0001) according to log-rank (Mantel-Cox) test.

FIG. 4b is a graph indicating tumour weight for treatment with Alimta or Abraxane alone as compared to co treatment with Odeltamivir Phosphate.

Figure 1:
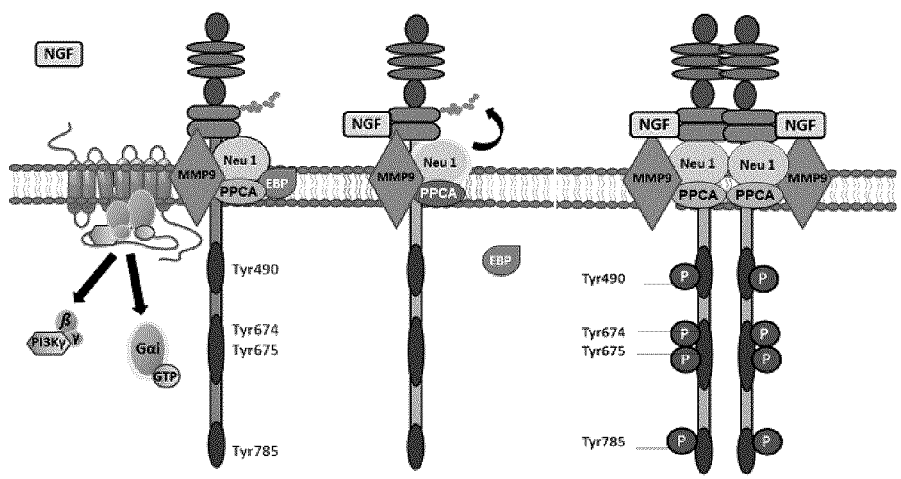
FIG. 1 is a schematic representing the cell surface receptor signalling pathway modulated by Neu1 sialidase.

(a) Control vs oseltamivir phosphate 2 and 5 mg/kg (p<0.0001)

(b) Control vs abraxane (p<0.09, not significant)

(c) Control vs abraxane, oseltamivir phosphate 2 and 5 mg/kg (p<0.0009)

(d) Control vs gemcitabine, oseltamivir phosphate 2 and 5 mg/kg (p<0.0001)

DETAILED DESCRIPTION OF THE INVENTION

As used herein, the following terms are used as defined below unless otherwise indicated:

"Anti-cancer agent", "chemotherapeutic agent", and "antineoplastic agent" have the same meaning, and these terms represent the drugs (medicaments) used to treat cancer.

"At least one" means one or more than one, e.g., 1, 2 or 3, or 1 or 2, or 1.

"Concurrently" represents (1) simultaneously in time (e.g., at the same time); or (2) at different times during the course of a common treatment schedule.

"Consecutively" means one following the other.

"Effective amount" or "therapeutically effective amount" is meant to describe an amount of compound or a composition of the present invention effective in inhibiting or treating cancer. For example, the amount of the compound or composition that results in: (a) the reduction, alleviation or disappearance of one or more symptoms caused by the cancer, (b) the reduction of tumour size, (c) the elimination of the tumour, (d) long-term disease stabilization (reduction of growth or growth arrest) of the tumour and/or (e) prevention of or reduction of metastasis.

"One or more" means at least one, e.g., 1, 2 or 3, 1 or 2, or 1.

"Patient" includes humans and animals (preferably, humans).

"Prodrug" represents compounds that are transformed, in vivo to the active compound or to a salt and/or to a solvate thereof. Prodrug forms would be known to one of skill in the art as taught in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Sequentially" means (1) administration of one component of the method ((a) compound of the invention, or (b) chemotherapeutic agent) followed by administration of the other component or components; after administration of one component, the next component can be administered substantially immediately after the first component, or the next component can be administered after an effective time period after the first component; the effective time period is the amount of time given for realization of maximum benefit from the administration of the first component.

"Solvate" means a physical association of a compound with one or more solvent molecules; This physical association involves varying degrees of ionic and covalent bonding, including hydrogen bonding; In certain instances the solvate will be capable of isolation, for example when one or more solvent molecules are incorporated in the crystal lattice of the crystalline solid; "Solvate" encompasses both solution-phase and isolatable solvates; Non-limiting examples of suitable solvates include ethanolates, methanolates, and the like; "Hydrate" is a solvate wherein the solvent molecule is water.

"Pharmaceutical composition" is intended to encompass both the bulk composition and individual dosage units comprised of one or more (e.g., two) pharmaceutically active agents such as, for example, a compound of the present invention and an additional agent such as a chemotherapeutic agent, along with any pharmaceutically suitable carrier. The bulk composition and each individual dosage unit can contain fixed amounts of the aforementioned one or more pharmaceutically active agents. The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition or individual dosage units.

"Subject" is intended to include animals, which are capable of suffering from or afflicted with a disease disclosed herein (e.g., cancer). Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer.

"Carrier" refers to, for example, a diluent, adjuvant, excipient, auxilliary agent or vehicle which may be combined with an active agent of the present invention. A "pharmaceutically acceptable carrier", or "pharmaceutically suitable carrier" refers to a carrier suitable for administration to a subject.

For example, pharmaceutical carriers suitable for injection can include but are not limited to sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treatment" can also mean prolonging survival as compared to expected survival if not receiving treatment.

"Analogue" as in "oseltamivir analogue" refers to an analogue of oseltamivir that is a Neu1 inhibitor and further refers to an analogue that is effective as a anti cancer agent. Such analogues may include derivatives of oseltamivir or intermediates useful for the preparation of oseltamivir.

Methods of Treatment

According to one aspect, the present invention provides a method for inhibiting or treating proliferative disease more specifically cancer and more specifically cancer growth, progression, or metastasis by administering an effective amount (e.g., a therapeutically effective amount) of oseltamivir phosphate to a patient in need of such treatment. In an embodiment, the invention provides a method for inhibiting or treating the growth of tumours by the administration of an effective amount (e.g., a therapeutically effective amount) of oseltamivir phosphate.

Examples of proliferative diseases (i.e., cancers) that may be inhibited or treated include, but are not limited to: lung cancer (e.g., lung adenocarcinoma and non small cell lung cancer); pancreatic cancers (e.g., pancreatic carcinoma such as, for example, exocrine pancreatic carcinoma); stomach cancers, esophageal cancers, colon cancers (e.g., colorectal carcinomas, such as, for example, colon adenocarcinoma and colon adenoma); myeloid leukemias (for example, acute myelogenous leukemia (AML), chronic myelogenous leukemia (CML), and chronic myelomonocytic leukemia (CMML); thyroid follicular cancer; myelodysplastic syndrome (MDS); bladder carcinoma; epidermal carcinoma; melanoma; breast cancer; prostate cancer; head and neck cancers (e.g., squamous cell cancer of the head and neck); ovarian cancer; brain cancers (e.g., gliomas); cancers of mesenchymal origin (e.g., fibrosarcomas and rhabdomyosarcomas sarcomas; tetracarcinomas; neuroblastomas) bone cancer, kidney carcinomas; hepatomas; Non-Hodgkin's lymphoma; multiple myeloma); and anaplastic thyroid carcinoma.

For example, embodiments of this invention include methods of treating cancer, wherein said cancer is: pancreatic cancers, stomach cancers, esophageal cancers, lung cancers, myeloid leukemias, thyroid follicular tumours, myelodysplastic syndrome, head and neck cancers, melanomas, breast cancers, prostate cancers, ovarian cancers, bladder cancers, gliomas, epidermal cancers, colon cancers, non-Hodgkin's lymphomas, or multiple myelomas, comprising administering to said subject in need of such treatment, an effective amount of oseltamivir phosphate.

In particular embodiments, oseltamivir phosphate can be used to treat pancreatic cancer, breast cancer, or ovarian cancer in a subject in need thereof.

In a particular embodiment the subject is a mammal in a further embodiment the subject is human.

In a further aspect, the invention provides methods for inhibiting or treating proliferative diseases particularly cancer, and more particularly refractory cancers.

The term refractory describes a disease or condition that does not respond to treatment. In particular, the refractory cancer may be a cancer that is or has become drug resistant.

Neu1 sialidase an enzyme which cleaves α-2,3-linked sialic acids from the glycosylated cellular molecules has been implicated as a critical mediator of TrkA and TrkB and receptor activation upon ligand binding to the receptor in both live primary neurons and TrkA/B-expressing cell lines. Studies suggest that once the ligand binds to the Trk receptor, Neu1 sialidase becomes activated via a GPCR and matrix metalloproteinase (MMP)-mediated pathway. Upon activation the sialidase functions to desialylate the external receptor this leads to dimerization, and thus receptor activation and subsequent signaling, as depicted in FIG. 1.

It has been further found that Trk A receptor and EGFR are activated through a corresponding membrane signaling paradigm. It is believed that inhibition of Neu1 sialidase inhibits this pathway thereby inhibiting the activity of at least these receptors.

Given that receptor desialylation by Neu1 has been shown to be an important step in TrkA [12], insulin and insulin-like growth factors [29], and epidermal growth factor receptor activation and signalling, Neu1 sialidase may in fact act as a master common enzyme in the activation of all RTK receptors.

While not wishing to be bound by theory, it is believed that oseltamivir phosphate acting as a Neu1 sialidase inhibitor inhibits the signaling pathway for activating receptors including TrkA receptor and EGFR which are known to play a role in the growth and proliferation of cancer. The use of oseltamivir phosphate to inhibit Neu1 sialidase and to thereby inhibit the signaling pathway for activating receptors such as Trk A and EGFR may be applied as a treatment of proliferative diseases such as cancer.

Without wishing to be bound by theory, it is believed that oseltamivir phosphate may function through the inhibition of Neu1 sialidase to inhibit the pathway that modulates a number of receptors and the down stream pathways of those receptors which are implicated in cancer growth and/or proliferation.

Analogues of Oseltamivir

In another embodiment of the invention analogues of oseltamivir have been found to act as Neu1 sialidase inhibitors thereby inhibiting the signaling pathway in a corresponding manner to oseltamivir phosphate. These analogues of oseltamivir have also been found to show activity as anti-cancer agents in in vitro studies. Accordingly, an embodiment of the invention is directed to methods of treating cancer comprising administering to a subject in need thereof an analogue of oseltamivir phosphate.

In an embodiment of the invention the analogues of oseltamivir are analogues of oseltamivir that are Neu1 sialidase inhibitors. In a further embodiment the analogues are selected from analogues described as derivatives of oseltamivir phosphate and intermediates for the preparation of oseltamivir phosphate disclosed in PCT published applications WO2009/137916 and WO2011/047466.

In an embodiment of the invention an analogue of oseltamivir is a compound according to any one of formulas A-F:

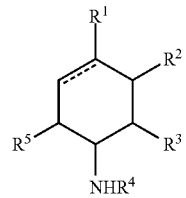

Formula A wherein, $R^1$ is halo or $COOR^6$;

$R^2$ is OH or $OR^7$;

$R^3$ is OH, $OR^8$ or $N_3$;

$R^4$ is H or $C_{1-6}$acyl;

$R^5$ is $OC_{1-6}$alkyl, $SC_{1-6}$alkyl, OH, SH, halo, $N_3$, $NH_2$, $NHC_{1-6}$alkyl or $NHPG^4$ or $R^4$ and $R^5$ are linked, together with the atoms to which they are attached, to form an oxazoline ring;

$R^6$ is $C_{1-6}$alkyl;

$R^7$ and $R^8$ are the same or different and are independently $C_{1-6}$alky, $C_{1-6}$ acyl or $PG^5$, or $R^7$ and $R^8$ are joined together with the oxygen atoms to which they are attached, to form a 5-membered cyclic ketal that is substituted on the carbon between the oxygen atoms by one or two $C_{1-6}$alkyl (preferably dimethy or diethyl ketal);

$PG^4$ and $PG^5$ are independently protecting groups.

----- represents a single or double bond and one or more hydrogens in the $C_{1-6}$alkyl and/or $C_{1-6}$acyl groups is/are optionally replaced with F;

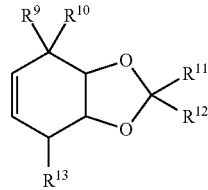

Formula B wherein $R^9$ is $COOR^{14}$ $R^{10}$ is H, OH or $OC_{1-6}$acyl;

$R^{13}$ is $NHC_{1-6}$acyl;

or the O in $R^{10}$ and the N in $R^{13}$ are joined by a covalent bond;

$R^{11}$ and $R^{12}$ are independently $C_{1-6}$alkyl;

$R^{14}$ is $C_{1-6}$alkyl, and one or more of the hydrogen atoms in the $C_{1-6}$alkyl and/or $C_{1-6}$acyl groups is/are optionally replaced with F;

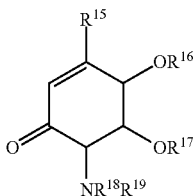

Formula C wherein,
$R^{15}$ is COOEt, COOMe, COOiPr, COOnPr, COOCH$_2$C≡CH, C(O)H, C(O)OH, C(O)O$^-$, CCl$_3$, CN, C≡CH, CH$_2$C≡CH or CH$_2$OH;
$R^{16}$ and $R^{17}$ are independently H, C$_{1-6}$alky, C$_{1-6}$acyl or a suitable protecting group, or $R^{16}$ and $R^{17}$ are joined to form a suitable protecting group such as, a cyclic ketal which may be optionally substituted on the carbon atom between the oxygen atoms by one or two C$_{1-6}$alkyl groups.
$R^{18}$ and $R^{19}$ are independently H, C$_{1-6}$alky, C$_{1-6}$acyl or a suitable protecting group or $R^{18}$ and $R^{19}$ are joined to form a suitable protecting group;
wherein one or more hydrogens in $R^{15}$, $R^{16}$, $R^{17}$ $R^{18}$ and/or $R^{19}$ is are optionally replaced with F;

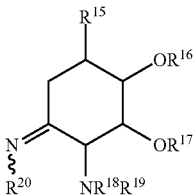

Formula D wherein,
$R^{15}$ is COOEt, COOMe, COOiPr. COOnPr, COOCH$_2$C≡CH, C(O)H, C(O)OH, C(O)O$^-$, CCl$_3$, CN, C≡CH, CH$_2$C≡CH or CH$_2$OH;
$R^{16}$ and $R^{17}$ are independently H, C$_{1-6}$alky, C$_{1-6}$acyl or a suitable protecting group, or $R^{16}$ and $R^{17}$ are joined to form a suitable protecting group such as, a cyclic ketal which may be optionally substituted on the carbon atom between the oxygen atoms by one or two C$_{1-6}$alkyl groups.
$R^{18}$ and $R^{19}$ are independently H, C$_{1-6}$alky, C$_{1-6}$acyl or a suitable protecting group or $R^{18}$ and $R^{19}$ are joined to form a suitable protecting group; and
$R^{20}$ is a group that is removed under reduction or hydrogenation reaction conditions or $R^{20}$ is a suitable acid labile protecting group, for example $R^{20}$ is OH, R, O—R, O(C)—R. Si(R)$_3$, NO$_2$, NH$_2$, N(R)$_2$, S(O)$_2$R or S(O)$_2$OR, wherein each R is independently alkyl, aryl or heteroaryl and various substituted derivatives thereof.
wherein one or more hydrogens in $R^{15}$, $R^{16}$, $R^{17}$ $R^{18}$, $R^{19}$ and/or $R^{20}$ is/are optionally replaced with F;

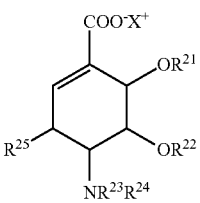

Formula E wherein,
X+ is a cation;
$R^{21}$ and $R^{22}$ are independently H, C$_{1-6}$alkyl or C$_{1-6}$acyl, or $R^{21}$ and $R^{22}$ are joined together with the atoms to which they are attached, to form a 5-10-membered ring that is unsubstituted or substituted with one or more halo or C$_{1-6}$alkyl;
$R^{23}$ and $R^{24}$ are independently H, C$_{1-6}$alkyl and C$_{1-6}$acyl;
$R^{25}$ is OR$^{26}$, NR$^{27}$R$^{28}$, =O or =NR$^{29}$;
$R^{26}$ is H, C$_{1-6}$alkyl or C$_{1-6}$acyl;
$R^{27}$ and $R^{28}$ are independently H, C$_{1-6}$alkyl or C$_{1-6}$acyl;
$R^{29}$ is H, OH, C$_{1-6}$alkyl, OC$_{1-6}$alkyl, C$_{1-6}$acyl, OC$_{1-6}$acyl, NH$_2$, NHC$_{1-6}$alkyl, N(C$_{1-6}$alkyl)(C$_{1-6}$acyl or NHC$_{1-6}$acyl, or $R^{29}$ and one of $R^{23}$ and $R^{24}$ form a linker group "-A-C(O)—" to provide a compound of the formula:

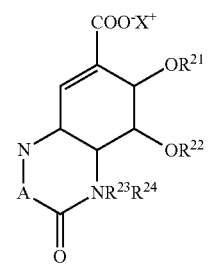

wherein A is O or NH; and
one or more available hydrogens in $R^{21}$, $R^{22}$, $R^{23}$, $R^{24}$, $R^{25}$, $R^{26}$, $R^{27}$, $R^{28}$ and/or $R^{29}$ is/are optionally replaced with F; or

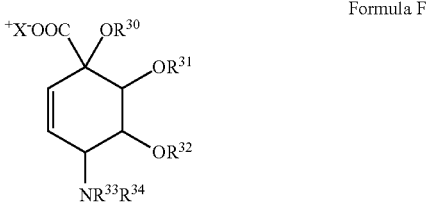

Formula F wherein,
X+ is a cation
$R^{30}$ is H, C$_{1-6}$alkyl or C$_{1-6}$acyl;
$R^{31}$ and $R^{32}$ are independently F, C$_{1-6}$alkyl or C$_{1-6}$acyl or $R^{31}$ and $R^{32}$ are joined together, with the atoms to which they are attached, to form a 5-10-membered ring that is unsubstituted or substituted with one or more of halo or C$_{1-4}$alkyl;
$R^{33}$ and $R^{34}$ are independently H, C$_{1-6}$alkyl or C$_{1-6}$acyl; and one or more available hydrogen atoms in $R^{30}$, $R^{31}$, $R^{32}$, $R^{33}$ and/or $R^{34}$ is/are optionally replaced with F or salts, solvates, prodrugs, stereoisomers or isotope-labelled forms thereof or mixtures thereof.

In a further embodiment the compound is a compound of formula E and R25 is =NR$^{29}$.

In a further aspect of the invention the analogue is:

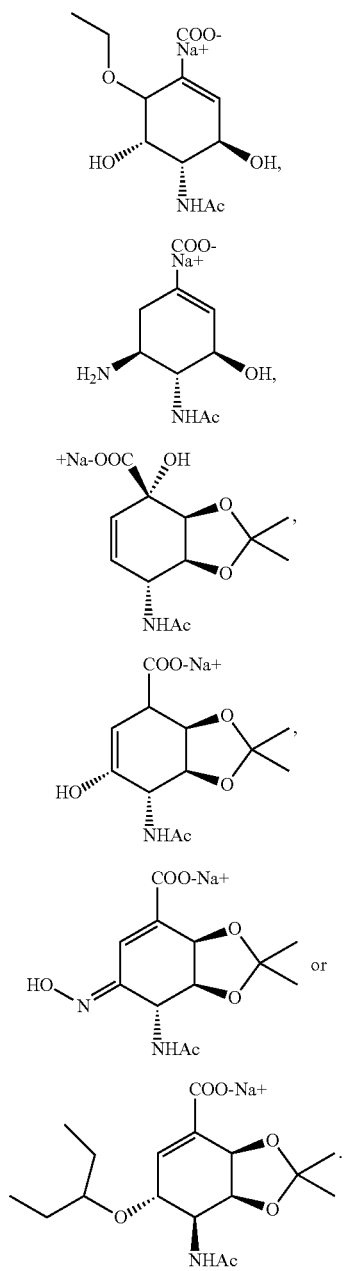

In still a further aspect the corresponding chemical names for the above structure are:

Sodium; 4-acetylamino-6-ethoxy-3,5-dihydroxy-cyclohex-1-enecarboxylate (A1); Sodium; 4-acetylamino-5-amino-3-hydroxy-cyclohex-1-enecarboxylate (A2);

Sodium; 7-acetylamino-4-hydroxy-2,2-dimethyl-3a,4,7,7a-tetrahydro-benzo[1,3]dioxole-4-carboxylate (A3);

Sodium; 7-acetylamino-6-hydroxy-2,2-dimethyl-3a,4,7,7a-tetrahydro-benzo[1,3]dioxole-4-carboxylate (A4);

Sodium; 7-acetylamino-6-hydroxyimino-2,2-dimethyl-3a,6,7,7a-tetrahydro-benzo[1,3]dioxole-4-carboxylate (A5) and Sodium; 7-acetylamino-6-(1-ethyl-propoxy)-2,2-dimethyl-3a,6,7,7a-tetrahydro-benzo[1,3]dioxole-4-carboxylate (A6).

While the analogues described above are shown in the sodium salt form it will be understood by a person of skill in the art that other salt forms are possible and are included in the scope of the invention. Additionally, caboxylate ester of lower alkyl (C1-6 alkyl) forms are also included in the scope of the invention "Alkyl" as used herein, whether it is used alone or as part of another group means straight or branched chain saturated alkyl groups. "$C_{1-6}$alkyl" refers to an alkyl groups having 1, 2, 3, 4, 5 or 6 carbon atoms.

"Acyl" as used herein, whether it is used alone or as part of another group means straight or branched chain saturated acyl groups. "$C_{1-6}$acyl" refers to an acyl group having 1, 2, 3, 4, 5, or 6 carbon atoms.

"Halo" as used herein refers to a halogen atom and includes F, Cl, Br and I.

A wavy bond, such as, "~~~" indicates that the stereochemistry of the bond is variable. For example when attached to a double bond, this symbol indicates that the group bonded to the double bond is in either the cis or trans configuration or the compound comprises a mixture of the two configurations.

"Optionally substituted" as used herein means that the referenced group is unsubstituted or substituted with one or more groups, for example optional substituents may include $C_{1-6}$alkoxy, nitro, cyano, hydroxyl and amino, and protected forms thereof.

The term "pharmaceutically acceptable salt" means an acid addition salt or basic addition salt of a neutral compound, which is suitable for, or compatible with, the treatment of a subject.

The term "pharmaceutically acceptable acid addition salt" as used herein means any non-toxic organic or inorganic salt of any base compound of the invention, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the formula I, for laboratory use, or for subsequent conversion to a pharmaceutically acceptable acid addition salt. In embodiments of the invention, the pharmaceutically acceptable acid addition salt is the hydrochloride salt.

The term "pharmaceutically acceptable basic addition salt" as used herein means any non-toxic organic or inorganic salt of any acid compound or any of its intermediates. If a compound comprises an acidic group, for example a carboxylic acid, a basic addition salt is formed by adding a suitable base. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. Such salts may exist in either hydrated solvated or substantially anhydrous form. The selection of the appropriate salt will be known to one skilled in the art. In an embodiment of the invention the pharmaceutically acceptable basic addition salt is an alkali metal salt such as a sodium salt.

The formation of a desired compound salt is achieved using standard techniques. For example, the neutral compound is treated with an acid or base in a suitable solvent and the formed salt is isolated by filtration, extraction or any other suitable method.

The analogues of the invention may further be formulated as solvates. The term "solvate" refers to incorporation of molecules of a suitable solvent in the crystal lattice of a compound. A suitable solvent is physiologically tolerable at the dosage administered. Examples of suitable solvents are ethanol, water and the like. When water is the solvent, the molecule is referred to as a "hydrate". The formation of solvates of the analogues of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Analogues of oseltamivir as described above may further include prodrug forms. In general, such prodrugs will be functional derivatives of a compound of the formula I which are readily convertible in vivo into the compound from which it is notionally derived. Prodrugs of the anlaogues may be conventional esters formed with available hydroxy, or amino group. For example, an available OH or nitrogen in a compound may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the analogues are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The term "isotopic label" refers to an isotopic form of an atom that is other than the most abundant form of that atom in nature. For example $^2H$, $^3H$, $^{13}C$, $^{14}C$ or a radioactive halogen such as $^{125}I$. A labelled compound of the invention may be prepared using standard methods known in the art. For example, tritium may be incorporated into a compound using standard techniques, for example by hydrogenation of a suitable precursor to a compound of the invention using tritium gas and a catalyst. Alternatively, a compound containing a radioactive iodo may be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound may be prepared from the corresponding non-radioactive halo, suitable iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

Analogues of the invention may include protecting groups on various chemical moieties, substitution of the protecting group and/or deprotection of those chemical moieties would be known to a person of skill in the art and analogues containing such modifications would also be included in the scope of the invention.

The terms "protecting groups" or "protective groups" or "PG" or the like, refer to a chemical moiety which protects or masks a reactive portion of a molecule generally for the purpose of preventing side reactions in those reactive portions of the molecule while manipulating or reacting different portions of the molecule. After the manipulation or reaction is complete, the protecting group may be removed under conditions that do not degrade or decompose the remaining portions of the molecule. The selection of suitable protecting groups can be made by a person of skill in the art. Many conventional protecting groups are known in the art, for example as described in "Protective Groups in Organic Chemistry" McOmie, J. F. W. Ed. Plenum Press, 1973, In Greene, T. W. and Wuts, P. G. M., "Protective Groups in Organic Synthesis" John Wiley & Sons, $3^{rd}$ Edition, 1999 and in Kocienski, P. "Protecting Groups", $3^{rd}$ Edition, 2003, Georg Thieme Verlag (The Americas).

Analogues of the invention may include asymmetric centres. Where the analogues of the invention poses more than one asymmetric centre, they may exist as diastereomers. It is to be understood that all such isomers and mixtures thereof in any proportion are encompassed within the scope of the present invention. It is to be understood that while the stereochemistry of the compounds of the invention may be as provided for in any given compound listed herein, such compounds of the invention may also contain certain amounts (e.g. less than 20%, preferably less than 10%, more preferably less than 5%) of compounds of the invention having alternate stereochemistry.

It will be understood by a person of skill in the art that while the above embodiments serve as specific examples of oseltamivir analogues that are active as Neu1 inhibitors and anti-cancer agents, additional analogues of oseltamivir including those that have been disclosed in the WO 2009/137916, and WO 2011/047466 may also be suitable Neu1 inhibitors and anti-cancer agents. Such analogues are to be considered as being within the scope of the claimed invention.

Administration Forms

In another aspect of the present invention, pharmaceutical compositions are provided, which comprise oseltamivir phosphate and/or an analogue of oseltamivir phosphate, and optionally comprise a pharmaceutically acceptable carrier. After formulation with an appropriate pharmaceutically acceptable carrier in a desired dosage, the pharmaceutical compositions of this invention can be administered to a subject orally, rectally, parenterally, intracisternally, intravaginally, intraperitoneally, topically (as by powders, ointments, or drops), bucally, as an oral or nasal spray, intramuscularly, intravenously or intratumourally or the like, depending on the cancer being treated.

In accordance with the methods of the invention, oseltamivir phosphate or an analogue of oseltamivir phosphate or a salts or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions will be formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilated edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringeability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the formula I and use the lypolizates obtained, for example, for the preparation of products for injection.

A variety of inactive adjuvant substances in tablets or capsules, to aid the dissolution of the compounds or modulate the timing of their release (e.g. in extended release formulations). Such ingredients may include but are not limited to high molecular weight polyethylene glycols or polyvinyl pyrrolidones (e.g. Povidone), which may be formulated with compounds of the invention in solid dispersions to enhance gastrointestinal solubility and/or dissolution rate. Compounds of the invention may also be administered orally in the form of solutions containing GRAS (Generally Regarded As Safe) vehicle components to aid dissolution, including but not limited to low molecular weight polyethylene glycols (PEGs), polyvinyl pyrrolidones, sorbitol, mannitol and similar polyhydroxylated compounds, carboxymethyl cellulose, dextranes, etc. Such dissolution aids may also be employed in liquid formulations for intravenous infusion.

Liquid dosage forms for oral administration include, but are not limited to, pharmaceutically acceptable emulsions, micro-emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), cremaphor, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavouring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders, such as starches, lactose, sucrose, glucose, mannitol, and silicic acid, b) binders, such as, carboxymethylcellulose, alginates, gelatin, polyvinyl pyrrolidinone, sucrose, and acacia, c) humectants, such as, glycerol, d) disintegrating agents, such as, agar-agar, calcium carbonate, potato or tapioca starch, alginic acid, certain silicates, and sodium carbonate, e) solution retarding agents, such as, paraffin, f) absorption accelerators, such as, quaternary ammonium compounds, g) wetting agents, such as, cetyl alcohol and glycerol monostearate, h) absorbents, such as, kaolin and bentonite clay, i) lubricants, such as, talc, calcium stearate, magnesium stearate, solid polyethylene glycols, sodium lauryl sulfate, and mixtures thereof, and (j) dissolution rate enhancers, such as, high molecular weight polyethylene glycols or polyvinyl pyrrolidone in physical mixtures or in form of solid dispersions. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In certain embodiments, the oseltamivir phosphate of the invention may be administered at dosage levels of about 0.1 mg/kg to about 50 mg/kg, from about 1 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.1 mg/kg or greater than 50 mg/kg can be administered to a subject.

Administration of oseltamivir phosphate by injection can prevent or reduce the active phosphate from of the compound from being metabolized in the liver to the carboxylate form. Accordingly, in an embodiments of the invention, oseltamivir phosphate is administered by injection. In further embodiments the oseltamivir phosphate is administered intramuscularly, intravenously or intratumorally.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Preferably, polyethylene glycols or polyvinyl pyrrolidone are employed as solubilizing agents.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Method of Treatment, Combination Therapy

In a further aspect, the invention provides a method of treating cancer comprising administering an effective amount (e.g. a therapeutically effective amount) of oseltamivir phosphate and/or one or more analogues of oseltamivir phosphate to a subject in need of such treatment in combination with an effective amount of one or more anti-cancer agent (chemotherapeutic agents).

It will be understood that the examples of proliferative disease and of cancers described in relation to the method above may also be treated by this method of the invention.

In a further aspect of the invention the anti-cancer agent is a chemotherapeutic agent.

Examples of anti-cancer agents (i.e., chemotherapeutic agents) include anti-cancer agents selected from the group consisting of: taxanes, platinum coordinator compounds, epidermal growth factor (EGF) inhibitors that are antibodies, EGF inhibitors that are small molecules, vascular endothelial growth factor (VEGF) inhibitors that are antibodies, VEGF kinase inhibitors that are small molecules, MET inhibitors, ABL kinase inhibitors, ALK inhibitors, FLT-kinase inhibitors, MAPK/ERK kinase (MEK) inhibitors, RAF kinase inhibitors, farnesyl transferase inhibitors, estrogen receptor antagonists or selective estrogen receptor modulators (SERMs), anti-tumour nucleoside derivatives, epothilones, topoisomerase inhibitors, vinca alkaloids, antibodies that are inhibitors of integrins, small molecules that are inhibitors of integrins, folate antagonists, ribonucleotide reductase inhibitors, anthracyclines, biologics; thalidomide (or related imid), heat shock protein 90 inhibitors.

In one embodiment the invention provides a method of treating cancer comprising an effective amount of oseltamivir phosphate and/or one or more analogues of oseltamivir phosphate and an effective amount of a cis-platinum based chemotherapeutic agent, such as Cisplatin, Cisplatinum, or cis-diamminedichloroplatinum (II) (CDDP), fluorouracil, gemcitabine, tamoxifen, pemetrexed or a protein bound paclitaxel such as Abraxane.

In a further aspect of the invention it will be understood by one of skill in the art that the oseltamivir phosphate and/or one or more analogues of oseltamivir phosphate may be administered in combination with the best known standard treatment available for a particular type of cancer to improve or sustain the results of that treatment.

In a further aspect of the invention there is provided a method of treating a cancer that has become refractory to standard treatment comprising administering oseltamivir phosphate and/or one or more analogues of oseltamivir phosphate and the standard treatment for that cancer.

In another aspect of the invention there is provided a method of preventing a cancer from becoming refractory to a treatment regimen comprising administering oseltamivir phosphate and/or one or more analogues of oseltamivir phosphate with said treatment regimen.

In an embodiment, the invention provides a method of treating pancreatic cancer comprising administering to a subject in need thereof a therapeutically effective amount of oseltamivir and/or one or more analogues of oseltamivir phosphate and a therapeutically effective amount of gemcitabine.

In another aspect of the invention there is provided a method of treating cancer in a subject in need thereof comprising administering concurrently or sequentially oseltamivir phosphate and/or one or more analogues of oseltamivir phosphate and a chemotherapeutic agent as described above.

Embodiments of the methods of treatment of this invention are directed to the use of a combination of drugs (active agents) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The chemotherapeutic agents may be administered in the dosage forms that are readily available to the skilled clinician, and are generally administered in their normally prescribed amounts (as for example, the amounts described in the Physician's Desk Reference, 57th Edition, 2003 (published by Thompson P D R, Montvale, N.J. 07645-1742 the disclosure of which is incorporated herein by reference thereto), or the amounts described in the manufacture's literature for the use of the agent).

For example, the oseltamivir phosphate can be administered by injection, and the chemotherapeutic agents can be administered intravenously, usually as an IV solution. The use of a pharmaceutical composition comprising more than one drug is also within the scope of this invention.

The oseltamivir phosphate and/or one or more analogues of oseltamivir phosphate and the chemotherapeutic agents are administered in therapeutically effective dosages to obtain clinically acceptable results, e.g., reduction or elimination of symptoms or reduction or elimination of the tumor or slowing or prevention of further growth of the tumour.

Thus, the oseltamivir phosphate and/or one or more analogues of oseltamivir phosphate and chemotherapeutic agents can be administered concurrently or consecutively in a treatment protocol. The administration of the chemotherapeutic agents can be made according to treatment protocols already known in the art.

Treatment Protocol

The oseltamivir phosphate and chemotherapeutic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the oseltamivir phosphate may be administered in daily doses or in a weekly dose. The dosage amount may be modified based on frequency of administration. Dosing frequency may be modified based on the ease of access to treatment. For example patients in hospital may receive daily dosing, while patients outside the hospital may receive weekly or once every two to three week doses to coincide with administration of other chemotherapeutics. The chemotherapeutic agents are administered one or more times a week. Generally, chemotherapeutic agent is administered once a week or once every two or three weeks.

However, those skilled in the art will appreciate that treatment protocols can be varied according to the needs of the patient. Thus, the combination of active agents (drugs) used in the methods of this invention can be administered in variations of the protocols described above. For example, the oseltamivir phosphate can be administered discontinuously rather than continuously during the treatment cycle. Thus, for example, during the treatment cycle the oseltamivir phosphate can be administered daily for a week and then discontinued for a week, with this administration repeating during the treatment cycle. Or the oseltamivir phosphate can be administered daily for two weeks and discontinued for a week, with this administration repeating during the treatment cycle. Thus, the oseltamivir phosphate can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein oseltamivir phosphate is not dosed does not have to equal the number of days (or weeks) wherein the oseltamivir phosphate is dosed. Usually, if a discontinuous dosing protocol is used, the number of days or weeks that the oseltamivir phosphate is dosed are at least equal or greater than the number of days or weeks that the oseltamivir phosphate is not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week or a number of days, no dosing for a week or a number of days, with the pattern repeating during the treatment cycle.

The chemotherapeutic agents used with the oseltamivir phosphate are administered in their normally prescribed dosages during the treatment cycle (i.e., the chemotherapeutic agents are administered according to the standard of practice for the administration of these drugs).

Those skilled in the art will recognize that the actual dosages and protocols for administration employed in the methods of this invention may be varied according to the judgment of the skilled clinician. A determination to vary the dosages and protocols for administration may be made after the skilled clinician takes into account such factors as the patient's age, condition and size, as well as the severity of the cancer being treated and the response of the patient to the treatment.

The oseltamivir phosphate in any of the above described treatment protocols may be replaced with one of more analogues of oseltamivir phosphate, or one or more analogues of oseltamivir phosphate may be added to the treatment protocol.

Other Neu1 Sialidase Inhibitors.

In another aspect of the invention it has been found that the antiviral compound 2-deoxy-2,3-dehydro-N-acetyl-neuraminic acid (DANA) is a moderate inhibitor of Neu1 sialidase. It has also been found that analogues of DANA are inhibitors of Neu1 sialidase. Neu1 inhibitors DANA and the analogues thereof are believed to be useful in the treatment of cancer based on their activity as Neu1 sialidase inhibitors and the mechanism which has been shown to link the inhibition of Neu1 sialidase with the modulation of Trk receptor, EGFR and other receptors through the receptor signaling paradigm described above.

In an embodiment of the invention the analogues of DANA are of the Formula G

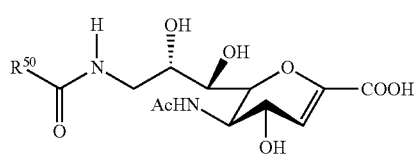

G

Wherein $R^{50}$ is $C_{1-6}$alkyl wherein the alkyl may be straight or branched aliphatic or the alkyl group may be a cyclic alkyl group.

In particular, $R^{50}$ is methyl, propyl butyl, cyclopropyl, cyclopentyl, cyclohexyl, 2 butyl, i-butyl, t-butyl, 3-pentyl, i-propyl.

In a particular aspect of the invention R is methyl, propyl, butyl, 2-butyl, cylopentyl, cyclohexyl.

In an embodiment of the invention the DANA analogue is:

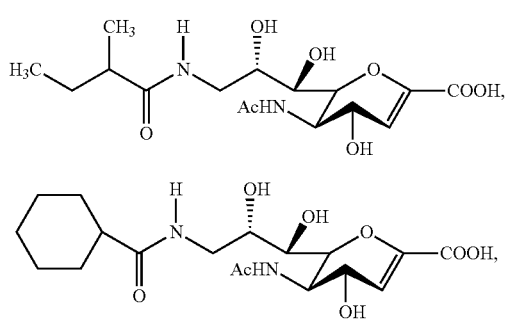

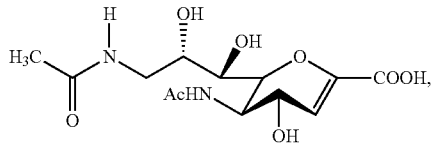

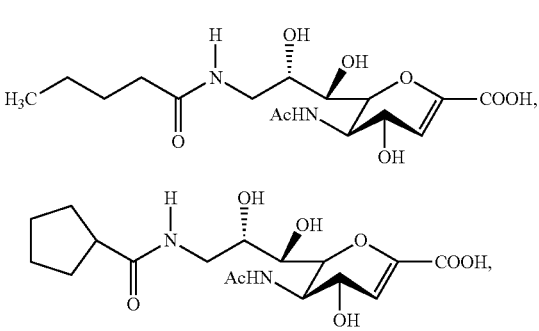

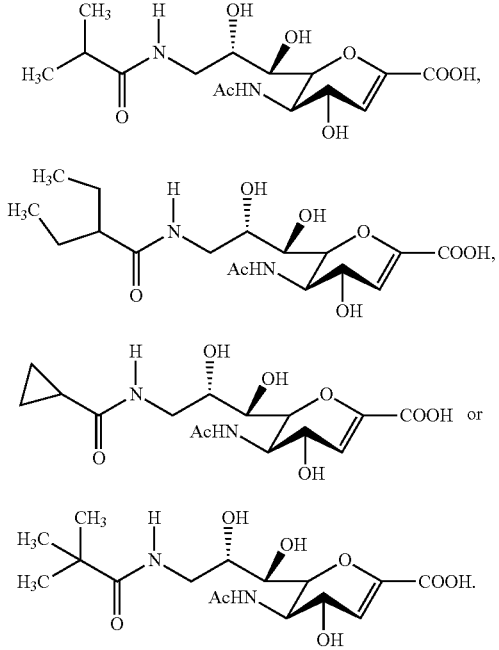

Kit

A further aspect of the invention provides a kit wherein the kit comprises a) a pharmaceutical composition of oseltamivir phosphate and a pharmaceutically acceptable carrier and b) instructions describing the method of using the pharmaceutical composition for treating cancer.

A further aspect of the invention provides a kit wherein the kit comprises a) one or more analogues of oseltamivir phosphate and b) instructions for use in treating cancer. In a further aspect of the invention the kit further comprises one or more chemotherapeutic agents.

Embodiments of the invention will now be described by way of examples.

Materials and Methods

Mice

An immunodeficient mouse model with a double mutation in the combining recombinase activating gene-1 or -2 (RAG1 or RAG2) and common cytokine receptor γ chain (cγ) were used as xenograft mice. The RAG2$^{-/-}$xcγ$^{-/-}$ double mutant mice on a Balbc genetic background are completely alymphoid (T-cell, B-cell, and NK-cell deficient), show no spontaneous tumour formation, and exhibit normal hematopoietic parameters. Mice deficient in both RAG2 and cγ (RAG2-/-/cγ-/-) were generated by intercrossing and were maintained in SPF isolators in the Animal Care Facility, Queen's University, Kingston, Ontario K7L3N6, Canada. A colony was established in the animal facility. Mice deficient in both RAG1 and cγ (RAG1$^{-/-}$×cγ$^{-/-}$) on a non-obese diabetic (NOD) genetic background were obtained from the Jackson Laboratory (Bar Harbor, Me.) and a colony was established in the animal facility. All mice were kept under sterile conditions in micro-isolators or air-filtered cages, and were provided with autoclaved food and water. All mice used in the studies were approved by the Animal Care Committee, Queen's University. They were used between 6 and 8 weeks of age.

Cancer Cell Lines

BxPC-3 cells (ATCC® Number: CRL-1687™) are human tumorigenic pancreatic cancer cell line with epithelial morphology expressing the 17 beta-estradiol (E2)-binding estrogen receptor and derived from a female patient with adenocarcinoma (a cancer of an epithelium that originates in glandular tissue). Mia-PaCa-2 cells (ATCC® Number: CRL-1420™) are human pancreatic cancer cell line with attached epithelial and with floating rounded cells expressing the 17 beta-estradiol (E2)-binding estrogen receptor and derived from a male patient with carcinoma (cancer that begins in a tissue). PANC-1 cells (ATCC® Number: CRL-1469™) are human pancreatic cancer cell line with adherent epithelial morphology expressing no estrogen receptor and derived from ductal pancreas with epithelioid carcinoma. CAPAN-1 cells (ATCC® Number: HTB-79™) are human pancreatic cancer cell line with epithelial morphology expressing the 17 beta-estradiol (E2)-binding estrogen receptor and derived from metastatic liver with adenocarcinoma.

MDA MB-231cells (ATCC® Number: HTB-26™) are human mammary gland breast adenocarcinoma derived from metastatic pleural effusion with epithelial morphology. MCF-7 (ATCC® Number: HTB-22™) are human mammary gland breast adenocarcinoma derived from metastatic pleural effusion with epithelial morphology.

A-2780 cells are human ovarian cancer cell line which was established from tumor tissue from an untreated patient with adenocarcinoma. Cells grow as a monolayer and in suspension in spinner cultures. A-2780cis cells are the cisplatin-resistant A-2780 counterpart.

All cells were grown at 37° C. in 5% $CO_2$ in culture media containing Dulbecco's Modified Eagle Medium (DMEM) (Gibco, Rockville, Md.) supplemented with 10% fetal calf serum (FCS) (HyClone, Logan, Utah, USA).

eGFP Lentifect Purified Lentivirus Particles

GeneCopoeia Lentifect™ Lentiviral Particles (Cat # LP-EGFP-LV105-0205) are ready-to-use particles. They are produced from a standardized protocol using purified plasmid DNA and the proprietary reagents, EndoFectin™ Lenti (for transfection) and TiterBoost™ solution. The protocol uses a third generation self-inactivating packaging system meeting BioSafety Level 2 requirements. The Lentifect particles include a CMV promoter for efficient expression of non-tagged eGFP in target cells and use a puromycin resistance marker for selection of stably transduced cells. Ready-to-use lentiviral particles were used for the transduction of MiaPaCa-2 and PANC-1 cells.

Briefly, cells were cultured in 6 well tissue culture plates in DMEM medium containing 10% fetal calf serum (FCS) and 5 μg/mL plasmocin. After 24 hrs, medium was discarded and 2 mL of 5 μg/mL of polybrene media was added to the cells followed by eGFP lentiviral particles at MOI=6. The plate was mixed, centrifuged at 2500 rpm for 90 min. and incubated at 37° C. in 5% $CO_2$ humidified incubator for 24 hrs. The cells were washed and re-cultured in media for additional 2 days. On day 5, the media was replaced with selection media containing optimal 2 μg/mL of puromycin as pre-determined in a cell viability assay. Selection media was added every 40 hrs to expand puromycin-resistance eGFP transduced MiaPaCa-2 and PANC-1 cell clones. The transfection efficiency of 90% was determined using fluorescence microscopy (Zeiss Imager M2) and biophotonic imaging before implantation into the mice.

Cancer Cell Implantation into RAG-1$^{-/-}$ or RAG-2$^{-/-}$×cγ$^{-/-}$ Double Mutant Xenograft Mice Puromycin-resistance eGFP transduced MiaPaCa-2 or PANC-1 cell clones were grown in 75 $cm^2$ cell culture flask at 80% confluence. The cells were resuspended into solution using TrypLE Express (Gibco) and washed with sterile saline. The cell suspension was centrifuged for 3 min at 900 rpm, and the cell pellet resuspended in sterile saline at a concentration of 5-10×$10^6$ cells/mL for 1-2×$10^6$ cells implantation into the right back flank of the mouse. Tumour measurements were taken twice a week. Tumour volumes were determined by (width square/2)×length.

MTT Assay

MTT is a colorimetric assay for measuring the activity of enzymes that reduce MTT or closely related dyes (XTT, MTS, WSTs) to formazan dye, giving a purple color. A main application allows the assessment of the viability (cell counting) and the proliferation of cells (cell culture assays). It can also be used to determine cytotoxicity of potential medicinal agents and toxic materials, since those agents would stimulate or inhibit cell viability and growth. MTT (3-(4,5-Dimethylthiazol-2-yl)-2,5-diphenyltetrazolium bromide, a yellow tetrazole), is reduced to purple formazan in living cells. A solubilization solution (usually either dimethyl sulfoxide, an acidified ethanol solution, or a solution of the detergent sodium dodecyl sulphate in diluted hydrochloric acid) is added to dissolve the insoluble purple formazan product into a coloured solution. The absorbance of this coloured solution can be quantified by measuring at a certain wavelength (usually between 500 and 600 nm) by a spectrophotometer. The absorption maximum is dependent on the solvent employed.

The Cell Proliferation Reagent WST-1

WST-1 (Roche Applied Sciences, Montreal) is a ready-to-use substrate which measures the metabolic activity of viable cells. The WST-1 assay is nonradioactive and can be performed entirely in a microplate. It is suitable for measuring cell proliferation, cell viability or cytotoxicity. The assay is based on the reduction of WST-1 by viable cells. The reaction produces a soluble formazan salt. The procedure involves: Culturing the cells in a 96-well microplate, then incubating them with WST-1 for approx. 0.5-4 h. During this incubation period, viable cells convert WST-1 to a water-soluble formazan dye. Quantitating the formazan dye in the microplate is done with an ELISA plate reader. The absorbance directly correlates with the cell number.

Chemotherapeutics

Cisplatin, cisplatinum, or cis-diamminedichloroplatinum (II) (CDDP) is a platinum-based chemotherapy drug used to treat various types of cancers, including sarcomas, some carcinomas (e.g. small cell lung cancer, and ovarian cancer), lymphomas, and germ cell tumors. It was the first member of a class of anti-cancer drugs which now also includes carboplatin and oxaliplatin. These platinum complexes react in vivo, binding to and causing crosslinking of DNA which ultimately triggers apoptosis (programmed cell death).

Fluorouracil (5-FU or f5U) (sold under the brand names Adrucil, Carac, Efudex and Fluoroplex) is a drug that is a pyrimidine analog which is used in the treatment of cancer. It works through noncompetitive inhibition of thymidylate synthase. Due to its noncompetitive nature and effects on thymidine synthesis, 5-FU is frequently referred to as the "suicide inactivator". It belongs to the family of drugs called antimetabolites. It is typically administered with leucovorin.

Gemcitabine is used in various carcinomas: non-small cell lung cancer, pancreatic cancer, bladder cancer and breast cancer. It is being investigated for use in oesophageal cancer, and is used experimentally in lymphomas and various other tumour types. Gemcitabine represents an advance in pancreatic cancer care. It is also not as debilitating as some other forms of chemotherapy. As with fluorouracil and other analogues of pyrimidines, the triphosphate analogue of gemcitabine replaces one of the building blocks of nucleic acids, in this case cytidine, during DNA replication. The process arrests tumour growth, as new nucleosides cannot be attached to the "faulty" nucleoside, resulting in apoptosis.

Tamoxifen competitively binds to estrogen receptors on tumors and other tissue targets, producing a nuclear complex that decreases DNA synthesis and inhibits estrogen effects. It is a nonsteroidal agent with potent anti-estrogenic properties which compete with estrogen for binding sites in breast and other tissues. Tamoxifen causes cells to remain in the G0 and G1 phases of the cell cycle. Because it prevents (pre)cancerous cells from dividing but does not cause cell death, tamoxifen is cytostatic rather than cytocidal. Tamoxifen is a prodrug, having relatively little affinity for its target protein, the estrogen receptor. It is metabolized in the liver by the cytochrome P450 isoform CYP2D6 and CYP3A4 into active metabolites such as 4-hydroxytamoxifen and N-desmethyl-4-hydroxytamoxifen (endoxifen) which have 30-100 times more affinity with the estrogen receptor than tamoxifen itself. GPR30 is an estrogen-responsive GPCR (7-transmembrane G protein-coupled receptor). GPR30 is a 7-transmembrane G protein-coupled receptor (GPCR) that has been shown to be an estrogen responsive receptor, expressed predominantly in the endoplasmic reticulum. Signalling occurs via heterotrimeric G protein activation resulting in matrix-metalloproteinase activation, release of heparin-binding EGF and transactivation of EGFR with subsequent MAPK and Akt activation. Tamoxifen acts differentially on GPR30- and ER-mediated nuclear signal transduction and that tamoxifen activates GPR30 in a spatially different manner from estrogen.

Pemetrexed (brand name Alimta) is a chemotherapy drug manufactured and marketed by Eli Lilly and Company. Its indications are the treatment of Pleural Mesothelioma as well as non-small cell lung cancer. Pemetrexed is chemically similar to folic acid and is in the class of chemotherapy drugs called folate antimetabolites. It works by inhibiting three enzymes used in purine and pyrimidine synthesis: thymidylate synthase (TS), dihydrofolate reductase (DHFR), and glycinamide ribonucleotide formyltransferase (GARFT). By inhibiting the formation of precursor purine and pyrimidine nucleotides, pemetrexed prevents the formation of DNA and RNA, which are required for the growth and survival of both normal cells and cancer cells.

ABRAXANE for Injectable Suspension (paclitaxel protein-bound particles for injectable suspension) (albumin bound) is indicated for the treatment of breast cancer after failure of combination chemotherapy for metastatic disease or relapse within 6 months of adjuvant chemotherapy.

Oseltamivir phosphate was prepared from commercially available tablets of oseltamivir phosphate sold as Tamiflu. Tamiflu 75 mg capsules were solubilized in sterile saline and the non-dissolved filler discarded.

Statistics

Comparisons between two groups were made by one-way ANOVA at 95% confidence using unpaired t-test and Bonferroni's Multiple Comparison Test or Dunnett's Multiple Comparison Test for comparisons among more than two groups.

Example 1

$LD_{50}$ Values for the Effects of Oseltamivir Phosphate on the Cell Viability of Pancreatic, Breast and Ovarian Cancer Cells in Culture The data in Table 1 indicate the individual dose of oseltamivir phosphate treatment of pancreatic, breast and ovarian cancer cell lines in culture that is required to kill 50 percent of viable cells ($LD_{50}$). The $LD_{50}$ values are given as µM of drug concentration determined by MTT or WST-1 assay after 72 hrs of incubation. The results indicate that three pancreatic cancer cells (MiaPaCa-2, PANC-1 and BxPC-3) which are resistant to chemotherapeutics have high $LD_{50}$ values in the range of 850-1462 µM of oseltamivir phosphate treatment compared to the low $LD_{50}$ value of 2 µM of oseltamivir phosphate treatment of the chemo-sensitive Capan-1 pancreatic metastatic cancer cell line. In addition, two breast cancer cell lines (chemo-resistant MDA MB-231 and chemo-sensitive MCF-7) and two ovarian cancer cell lines (chemo-resistant A 2780cis and chemo-sensitive A 2780) following oseltamivir phosphate treatment showed low $LD_{50}$ values in the range of 0.6-3 µM. This in vitro data indicates that oseltamivir phosphate can reverse the resistance to chemotherapy in pancreatic, breast and ovarian cancer cell lines.

TABLE 1

$LD_{50}$ values for the effects of oseltamivir phosphate on the cell viability of cancer cells in culture

| Cancer | Cell line | Sensitivity to chemo-drugs | $LD_{50}$ (µM) |
| --- | --- | --- | --- |
| Pancreatic | MiaPaCa | resistant | 850 |
|  | PANC-1 | resistant | 1462 |
|  | BxPC-3 | resistant | 975 |
|  | Capan-1 | sensitive | 2 |
| Breast | MDA MB-231 | resistant | 0.6 |
|  | MCF-7 | sensitive | >3 |
| Ovarian | A 2780 | sensitive | 1.5 |
|  | A 2780cis | resistant | 1.0 |

$LD_{50}$ value is given as µM of drug concentration determined by MTT or WST-1 assay after 72 hrs of incubation. $LD_{50}$ represents the individual dose required to kill 50 percent of viable cells.

Oseltamivir phosphate used in combination with gemcitabine, cisplatin, 5-fluorouracil, and tamoxifen was shown to be effective particularly in cases where the cancer cells have become refractory to conventional chemotherapy (Tables 2-4). It is noteworthy that oseltamivir phosphate at 730 µM treatment of BxPC-3 cells used in combination with the indicated standard chemotherapeutic drugs increased the sensitivity ($LD_{50}$) of cisplatin by 5 fold-increase, 5-fluorouracil by 16, tamoxifen by 3 and gemcitabine by 1 (Table 2). Oseltamivir phosphate at 1460 µM treatment of BxCP-3 cells used in combination with the indicated standard chemotherapeutic drugs further increased the sensitivity of 5-fluoruracil by 160 fold-increase, tamoxifen by 115 and gemcitabine by 0.78. Similar trends of chemo-drug sensitivity with oseltamivir phosphate treatment are shown for PANC-1 (Table 3) and MiaPaCa-2 cells (Table 4).

TABLE 2

$LD_{50}$ values for the effects of oseltamivir phosphate (Tamiflu) co-treatment with standard chemotherapeutic drugs on the cell viability of cancer cells in culture

| Cancer | Cell lines | Chemo-drug | Oseltamivir phosphate Dosage (μM) | Chemo-drug $LD_{50}$ (μM) | Chemo-drug sensitivity with oseltamivir phosphate (fold increase) |
|---|---|---|---|---|---|
| Pancreatic | BxPC-3 | cisplatin | 0 | 4.2 | |
| | | cisplatin | 730 | 0.78 | 5 |
| | | 5-fluoruracil | 0 | 12.5 | |
| | | 5-fluoruracil | 730 | 0.78 | 16 |
| | | 5-fluoruracil | 1460 | 0.078 | 160 |
| | | tamoxifen | 0 | 9 | |
| | | tamoxifen | 730 | 3 | 3 |
| | | tamoxifen | 1460 | 0.078 | 115 |
| | | gemcitabine | 0 | 0.78 | |
| | | gemcitabine | 730 | 0.78 | 1 |
| | | gemcitabine | 1460 | 1 | 0.78 |

$LD_{50}$ value is given as μM of chemo-drug concentration with or without oseltamvir phosphate as determined by MTT assay after 72 hrs of incubation. $LD_{50}$ represents the individual dose required to kill 50 percent of viable cells.

TABLE 3

$LD_{50}$ values for the effects of oseltamivir phosphate (Tamiflu) co-treatment with standard chemotherapeutic drugs on the cell viability of cancer cells in culture

| Cancer | Cell lines | Chemo-drug | Oseltamivir phosphate Dosage (μM) | Chemo-drug $LD_{50}$ (μM) | Chemo-drug sensitivity with oseltamivir phosphate (fold increase) |
|---|---|---|---|---|---|
| Pancreatic | PANC-1 | cisplatin | 0 | >12 | |
| | | cisplatin | 730 | 6.25 | 2 |
| | | 5-fluoruracil | 0 | 3.1 | |
| | | 5-fluoruracil | 730 | 0.8 | 4 |
| | | 5-fluoruracil | 1460 | 0.078 | 40 |
| | | tamoxifen | 0 | 12.5 | |
| | | tamoxifen | 730 | 0.8 | 16 |
| | | tamoxifen | 1460 | 0.078 | 160 |
| | | gemcitabine | 0 | >26 | |
| | | gemcitabine | 730 | 1.6 | 16 |
| | | gemcitabine | 1460 | 1.5 | 17 |

$LD_{50}$ value is given as μM of chemo-drug concentration with or without oseltamivir phosphate as determined by MTT assay after 72 hrs of incubation. $LD_{50}$ represents the individual dose required to kill 50 percent of viable cells.

TABLE 4

$LD_{50}$ values for the effects of oseltamivir phosphate (Tamiflu) co-treatment with standard chemotherapeutic drugs on the cell viability of human cancer cells in culture

| Cancer | Cell lines | Chemo-drug | Oseltamivir phosphate Dosage (μM) | Chemo-drug $LD_{50}$ (μM) | Chemo-drug sensitivity with oseltamivir phosphate (fold increase) |
|---|---|---|---|---|---|
| Pancreatic | MiaPaCa-2 | cisplatin | 0 | 6.25 | |
| | | cisplatin | 730 | 0.8 | 8 |
| | | 5-fluoruracil | 0 | 2.20 | |
| | | 5-fluoruracil | 730 | 0.6 | 4 |
| | | 5-fluoruracil | 1460 | 0.078 | 28 |
| | | tamoxifen | 0 | 7.0 | |
| | | tamoxifen | 730 | 0.8 | 9 |
| | | tamoxifen | 1460 | 0.078 | 90 |
| | | gemcitabine | 0 | 0.78 | |
| | | gemcitabine | 730 | 0.78 | 1 |
| | | gemcitabine | 1460 | 0.078 | 10 |

$LD_{50}$ value is given as μM of chemo-drug concentration with or without Oseltamivir phosphate as determined by MTT assay after 72 hrs of incubation. $LD_{50}$ represents the individual dose required to kill 50 percent of viable cells.

The data shown in Table 5 indicate a 2 fold-increase in the $LD_{50}$ (μM) sensitivity of gemcitabine and abraxane chemotherapeutic drugs used in combination with 730 μM oseltamivir phosphate for pancreatic metastatic Capan-1 cells, two breast cancer cell lines (chemo-resistant MDA MB-231 and chemo-sensitive MCF-7) and two ovarian cancer cell lines (chemo-resistant A 2780cis and chemo-sensitive A 2780).

TABLE 5

$LD_{50}$ values for the effects of oseltamivir phosphate (Tamiflu) co-treatment with standard chemotherapeutic drugs on the cell viability of human cancer cells in culture

| Cancer | Cell lines | Chemo-drug | Oseltamivir phosphate Dosage (μM) | Chemo-drug $LD_{50}$ (μM) | Chemo-drug sensitivity with oseltamivir phosphate (fold increase) |
|---|---|---|---|---|---|
| Pancreatic | Capan-1 | gemcitabine | 0 | 60 | |
| | | gemcitabine | 730 | 30 | 2 |
| | | abraxane | 0 | 40 | |
| | | abraxane | 730 | 40 | 1 |
| Breast | MDA MB-231 | gemcitabine | 0 | 70 | |
| | | gemcitabine | 730 | 40 | 2 |
| | | abraxane | 0 | 40 | |
| | | abraxane | 730 | 29 | 1.4 |
| | MCF-7 | gemcitabine | 0 | 40 | |
| | | gemcitabine | 730 | 40 | 1 |
| | | abraxane | 0 | 40 | |
| | | abraxane | 730 | 18 | 2.2 |
| Ovarian | A 2780 | gemcitabine | 0 | 60 | |
| | | gemcitabine | 730 | 40 | 1.5 |
| | A 2780cis | gemcitabine | 0 | 60 | |
| | | gemcitabine | 730 | 40 | 1.5 |

$LD_{50}$ value is given as μM of drug concentration determined by WST-1 assay after 72 hrs of incubation. $LD_{50}$ represents the individual dose required to kill 50 percent of viable cells.

Example 2

$LD_{50}$ Values for the Effects of Oseltamivir Analogues on the Cell Viability of MiaPaCa-2 and PANG-1 Pancreatic Cancer Cells in Culture Oseltamivir analogues and methods of making same are disclosed in WO 2009/137916 and WO 2011/047466. -$LD_{50}$ values in μM for the effects of analogues on the cell viability of MiaPaCa-2 and Panc-1 pancreatic cancer cells in culture are shown in Table 6. The oseltamivir analogue A2 showed the highest potency with a $LD_{50}$ of 1.97 μM for MiaPaCa-2 cells and 0.01 μM for PANC-1 cells compared to oseltamivir phosphate of 850 μM for MiaPaCa-2 cells and 1462 μM for PANC-1 cells. The oseltamivir analogue with the next highest potency was A5 (24 μM for MiaPaCa-2 cells and 3 μM for PANC-1 cells) followed by A3, A1, A3 and A6 with decreasing potency in $LD_{50}$. This in vitro data establish the proof-of-concept that analogues of oseltamivir phosphate can also reverse the resistance to chemotherapy in pancreatic tumour cell lines (e.g. MiaPaCa and PANC-1).

TABLE 6

$LD_{50}$ values for the effects of oseltamivir phosphate analogues (TD) on the cell viability of MiaPaCa-2 and Panc-1 pancreatic cancer cells in culture

| TD Structure | $LD_{50}$ (μM) MiaPaCa-2 | PANC-1 |
|---|---|---|
| oseltamivir phosphate | 850 | 1462 |
| A1 | 132 | 848 |
| A3 | 2.1 | >1000 |
| A6 | >2000 | >2000 |
| A2 | 1.97 | 0.01 |
| A4 | 2.8 | 349 |
| A5 | 24 | 3 |

$LD_{50}$ value is given as μM of drug concentration determined by WST-1 assay after 72 hrs of incubation. $LD_{50}$ represents the individual dose required to kill 50 percent of viable cells.

Example 3

The Effect of Oseltamivir Phosphate at Different Dosage on Tumour Volume (mm³) on MiaPaCa-2-eGFP Pancreatic Cancer Cells Implanted in RAG2/Cγ Double Mutant Balbc Xenograft Mice The in vivo anti-tumour activity of oseltamivir phosphate was also investigated in a RAG2/Cγ double mutant xenograft male mouse model of human pancreatic cancer. MiaPaCa-2-eGFP pancreatic cancer cells at $1.5 \times 10^6$ in 0.2 mL were implanted subcutaneously in the right back flank of these mice. Each mouse in the study was identified by an ear punch number. Twice a week each mouse following implantation of the cancer cells was monitored for tumour volume growth (length and width) at the site of implantation, body weights, and body condition scoring. Scoring the body condition of rodents is a non-invasive method for assessing health and establishing endpoints for adults where body weight is not a viable monitoring tool, such as with tumour models. Body condition scores (BC) range from 1(emaciation) to 5 (obesity). An anticipated BCS of 2—under conditioned—or lower, requires justification in the protocol. Scores are determined by frequent visual and hands-on examination of each animal. The hands-on evaluation is done by gently holding the mouse by the base of the tail and passing a finger over the sacroiliac bones. The findings are matched to the descriptions and diagrams of BC ranges to determine a score. Scores are documented for each animal.

Figure 2A:
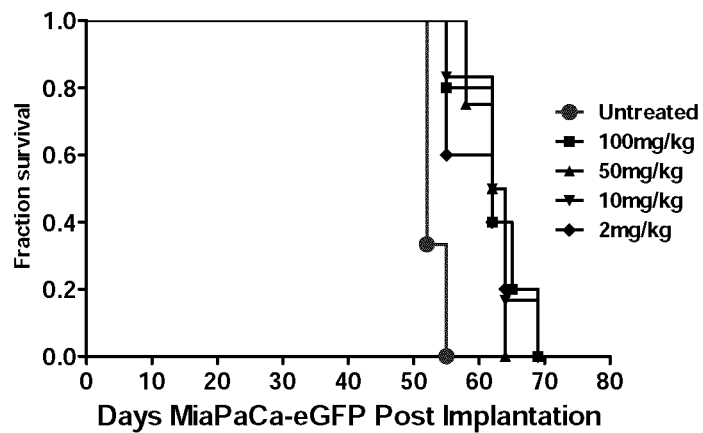
FIG. 2a shows survival rates of RAG2/Cγ double mutant mice implanted with MiaPaCa-2-eGFP pancreatic cancer cells following intraperitoneal treatment with different dosages of soluble oseltamivir phosphate. Survival curves are significantly different (p=0.0115) according to log-rank (Mantel-Cox) test.
Figure 2B:
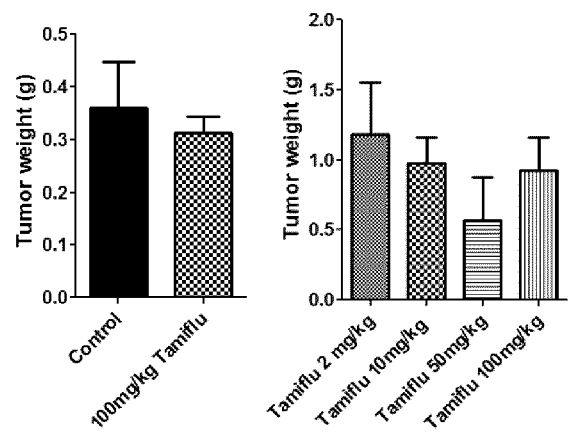
FIG. 2b shows graphs indicating the tumour weights (left graph day 48 and right graph day 61) for the treatment with different concentrations of oseltamivir phosphate.

The data in Table 7 show that 2, 10, 50 and 100 mg/kg of oseltamivir phosphate monotherapy treatment intraperitoneally at day 40 post implantation when the tumour volume was 50-100 mm$^3$ efficiently and significantly reduced tumour growth in a time-to-progression by over 50% and significantly extended the survival rates (FIG. 1) compared to the untreated control groups. In addition, there was a marked but not significant reduction in tumour weight compared to the untreated control cohort (FIG. 1). The monotherapy of oseltamivir phosphate treatment of RAG2/Cγ double mutant Balbc xenograft mice implanted with MiaPaCa-2-eGFP pancreatic cancer cells are reproducible using 50, 100 and 200 mg/kg dosages (Table 8 and FIG. 2). These findings support the hypothesis that oseltamivir phosphate monotherapy has potential anti-tumour proliferative properties in vivo and upholds the supporting evidence found in the in vitro results.

Alimta and Abraxane chemotherapeutic drugs against the growth and spread of pancreatic tumours was investigated. The RAG2/Cγ double mutant xenograft mouse model was implanted with 1.5×10$^6$ MiaPaCa-2-eGFP cells in 0.2 mL in the right back flank. When the tumour volume at the site of implantation reached 50-100 mm$^3$, mice were treated with Alimta at 100 mg/kg intraperitoneally (I.P.) for a total of 18 injections, 200 mg/kg Abraxane as a single injection I.P., or in combination with oseltamivir phosphate at 10 mg/kg I.P. daily. The data in Table 9 show that 10 mg/kg of oseltamivir phosphate in combination with Alimta or Abraxane efficiently reduced tumour growth in a time-to-progression at day 48 post implantation by 77% in combination with Almita and 94% with Abraxane compared with the control cohort. At day 63 post implantation, there was 40-75% reduction in the tumour volume with the combination treatment. At day 84 and 101 post implantation, the combination of Abraxane and oseltamivir phosphate maintained a 70% and 40% reduction, respectively, in tumour growth compared with the control cohort. In addition, Abraxane and oseltamivr phosphate combination significantly extended the survival rates of the tumour bearing mice by 101 days followed by Abraxane monotherapy at day 87, Alimta monotherapy and Alimta and oseltamivir phosphate combination at day 70 compared to the untreated control groups at day 51 (FIG. 3). In addition, there was a markedly but not significant reduction in tumour weight except for Abraxane monotherapy compared to the untreated control cohort (FIG. 3).

TABLE 7

The effect of oseltamivir phosphate dosage on tumour volume (mm$^3$) on MiaPaCa-2-eGFP pancreatic cancer cells implanted in RAG2/Cγ double mutant Balbc xenograft mice

| Days post Implantation | Dosage | untreated (n) | oseltamivir phosphate (n) | % Inhibition | p. value | (n) |
|---|---|---|---|---|---|---|
| 48 | 2 mg/kg | 965 ± 107 (10) | 370 ± 88 (5) | 61.7% | 0.0013 | (15) |
| 48 | 10 mg/kg | 965 ± 107 (10) | 275 ± 71 (6) | 71.5% | 0.0005 | (16) |
| 48 | 50 mg/kg | 965 ± 107 (10) | 383 ± 71 (4) | 60.3% | 0.0040 | (14) |
| 48 | 100 mg/kg | 965 ± 107 (10) | 397 ± 57 (5) | 58.9% | 0.0013 | (15) |
| 61 | 2 mg/kg | | 636 ± 35 (2) | 34.1% | 0.049 | (12) |
| 61 | 10 mg/kg | | 711 ± 159 (5) | 26.3% | ns | (15) |
| 61 | 50 mg/kg | | 652 ± 173 (3) | 32.4% | ns | (13) |
| 61 | 100 mg/kg | | 701 ± 201 (3) | 27.4% | ns | (13) |

TABLE 8

The effect of oseltamivir phosphate dosage on tumour volume (mm$^3$) on MiaPaCa-2-eGFP pancreatic cancer cells implanted in RAG2/Cγ double mutant Balbc xenograft mice

| Days post Implantation | Dosage | untreated (n) | oseltamivir phosphate (n) | % Inhibition | p value | (n) |
|---|---|---|---|---|---|---|
| 46 | 50 mg/kg | 930 ± 129 (8) | 368 ± 38 (4) | 60.4 % | 0.0040 | (12) |
| 46 | 100 mg/kg | 930 ± 129 (8) | 362 ± 62 (4) | 61.0 % | 0.0006 | (16) |
| 46 | 200 mg/kg | 930 ± 129 (8) | 386 ± 88 (4) | 58.5 % | 0.0081 | (12) |

The Effect of Co-Treatment of Oseltamivir Phosphate (10 mg/kg Daily) with Alimta (100 mg/kg 18 Injections) or Abraxane (200 mg/kg Single Injection) on Tumour Volume (mm$^3$) of MiaPaCa-2-eGFP Pancreatic Cancer Cells Implanted in RAG2/Cγ Double Mutant Balbc Xenograft Mice To assess the broad in vivo efficacy of 10 mg/kg dosage of oseltamivir phosphate in combination with standard

TABLE 9

The effect of co-treatment of oseltamivir phosphate (10 mg/kg daily) and Alimta (100 mg/kg) or Abraxane (200 mg/kg) on tumour volume (mm$^3$) on MiaPaCa-2-eGFP pancreatic cancer cells implanted in RAG2/Cγ double mutant Balbc xenograft mice

| Days post Implantation | Chemo-drug | Dosage (mg/kg) | Oseltamivir phosphate (mg/kg) | Tumour volume (mm$^3$) | % Inhibition To untreated |
|---|---|---|---|---|---|
| 48 | untreated | 0 | 0 | 809 | |
| 48 | alimta | 100 | 0 | 225 | 72% |
| 48 | alimta | 100 | 10 | 189 | 77% |
| 48 | abraxane | 200 | 0 | 201 | 75% |
| 48 | abraxane | 200 | 10 | 50 | 94% |
| 63 | alimta | 100 | 0 | 482 | 40% |
| 63 | alimta | 100 | 10 | 787 | 3% |
| 63 | abraxane | 200 | 0 | 358 | 56% |
| 63 | abraxane | 200 | 10 | 199 | 75% |

TABLE 9-continued

The effect of co-treatment of oseltamivir phosphate (10 mg/kg daily) and Alimta (100 mg/kg) or Abraxane (200 mg/kg) on tumour volume ($mm^3$) on MiaPaCa-2-eGFP pancreatic cancer cells implanted in RAG2/Cγ double mutant Balbc xenograft mice

| Days post Implantation | Chemo-drug | Dosage (mg/kg) | Oseltamivir phosphate (mg/kg) | Tumour volume ($mm^3$) | % Inhibition To untreated |
|---|---|---|---|---|---|
| 84 | abraxane | 200 | 0 | 864 | 0.06% |
| 84 | abraxane | 200 | 10 | 245 | 70% |
| 101 | abraxane | 200 | 10 | 487 | 40% |

The data in Table 10 indicate the liver metastases as a measure of the average number of nodules and nodule size in mm in each of the above treatment cohorts. There was a significant reduction in liver metastases by greater than 80% in the treated cohorts when compared to the untreated control. In addition, the combination of Almita or Abraxane with oseltamivir phosphate further reduced the liver metastases by 6% over the monotherapy of the chemotherapeutic drugs. The results in FIG. 4 show the biophotonic images of the different tissues obtained from necropsy. The black colour in the tissues is indicative of the presence of fluorescent MiaPaCa-2-eGFP cells.

TABLE 10

The effect of co-treatment of oseltamivir phosphate (10 mg/kg daily) and Alimta (100 mg/kg) or Abraxane (200 mg/kg) on liver metastases with MiaPaCa-2-eGFP pancreatic cancer cells implanted in RAG2/Cγ double mutant Balbc xenograft mice

| Days post implantation | Chemo-drug | Dosage (mg/kg) | Oseltamivir phosphate (mg/kg) | Liver Metastasis (avg no. nodules) | percent inhibition | Metastases (size, mm) |
|---|---|---|---|---|---|---|
| 51 | untreated | 0 | 0 | 33 | | 0.3-1.5 |
| 70 | Altima | 100 | 0 | 5 | 85% | 0.2-1.0 |
| 70 | Altima | 100 | 10 | 3 | 91% | 0.2-0.5 |
| 87 | Abraxane | 200 | 0 | 7 | 79% | 02.-0.7 |
| 101 | Abraxane | 200 | 10 | 5 | 85% | 0.3-1.0 |

The Effect of Co-Treatment of Oseltamivir Phosphate (100 mg/kg Daily) with Tamoxifen (0.1 mg/kg) on Tumour Volume ($mm^3$) of MiaPaCa-2-eGFP Pancreatic Cancer Cells Implanted in RAG2/Cγ Double Mutant Balbc Xenograft Mice To further assess the broad in vivo efficacy of 100 mg/kg dosage of oseltamivir phosphate in combination with standard tamoxifen chemotherapeutic against the growth and spread of pancreatic tumours was investigated. The RAG2/Cγ double mutant xenograft mouse model was implanted with $1.5 \times 10^6$ MiaPaCa-2-eGFP cells in 0.2 mL in the right back flank. When the tumor volume at the site of implantation reached 50-100 $mm^3$, mice were treated with tamoxifen at 0.1 mg/kg intraperitoneally (I.P.) for a total of 15 injections or in combination with oseltamivir phosphate at 100 mg/kg I.P., daily. The data in Table 11 show that 100 mg/kg of oseltamivir phosphate in combination with tamoxifen efficiently reduced tumour growth in a time-to-progression at day 59 post implantation by 43%, at day 62 by 56%, at day 66 by 47% and at day 73 by 17%.

TABLE 11

The effect of co-treatment of 100 mg/kg oseltamivir phosphate (Tamiflu) and 0.1 mg/kg Tamoxifen on tumour volume ($mm^3$) of MiaPaCa-2-eGFP pancreatic cancer cells implanted in RAG2/Cγ double mutant Balbc xenograft mice

| Days post Implantation | Treatment | Tumour volume ($mm^3$) | % Inhibition To untreated |
|---|---|---|---|
| 59 | untreated | 2214 ± 1288 (2) | |
| 59 | tamoxifen | 960 ± 208 (4) | 57% |
| 59 | tamoxifen + oseltamivir phosphate | 1266 ± 377 (4) | 43% |
| 62 | untreated | | |
| 62 | tamoxifen | 1738 ± 328 (4) | 21% |
| 62 | tamoxifen + oseltamivir phosphate | 984 ± 283 (3) | 56% |
| 66 | untreated | | |
| 66 | tamoxifen | 2650 ± 360 (3) | 0% |
| 66 | tamoxifen + oseltamivir phosphate | 1181 ± 180 (3) | 47% |
| 73 | untreated | | |
| 73 | tamoxifen | | |
| 73 | tamoxifen + oseltamivir phosphate | 1845 ± 5 (3) | 17% |

Figure 5:
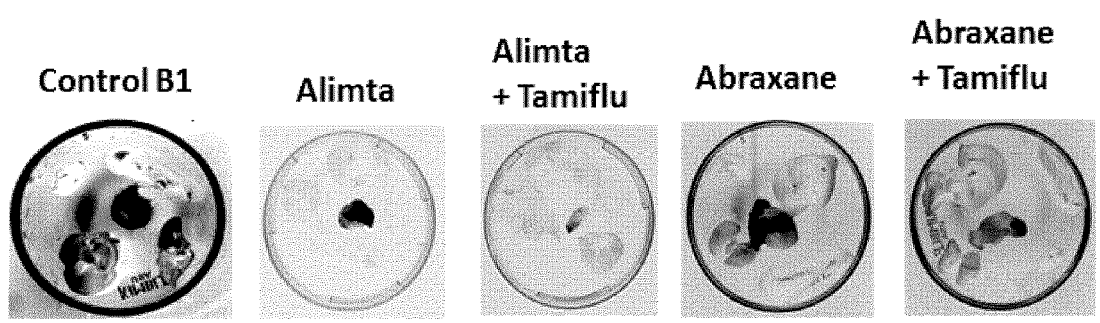
FIG. 5 Biophotonic images of tumour, spleen, liver, lungs, heart taken from MiaPaCa-2-eGFP pancreatic cancer cells implanted in RAG2/Cγ double mutant Balbc xenograft mice. The fluorescent MiaPaCa-2-eGFP cells in the tissues are indicated by black colour.

In addition, the combination of oseltamivir phosphate and tamoxifen significantly extended the survival rates of the tumour bearing mice by 76 days followed by tamoxifen monotherapy at day 66 compared to the untreated control groups at day 60 (FIG. 5).

The Effect of Co-Treatment of Oseltamivir Phosphate with Abraxane and Gemcitabine Chemotherapeutics on Tumour Volume ($mm^3$) of PANC-1 Human Pancreatic Cancer Cells Implanted in RAG1/Cγ Double Mutant NOD Xenograft Mice The in vivo efficacy of 2 or 5 mg/kg dosage of oseltamivir phosphate in combination with standard Abraxane and gemcitabine chemotherapeutics against the growth and spread of another pancreatic tumour was investigated using PANC-1 pancreatic cancer cells. The RAG1/Cγ double mutant xenograft mouse model was implanted with $2 \times 10^6$ PANC-1 cells in 0.2 mL in the right back flank. When the tumour volume at the site of implantation reached 50-100 $mm^3$, mice were treated with oseltamivir phosphate monotherapy at 2 and 5 mg/kg intraperitoneally (I.P.) daily injections, 0.5 mg/kg Abraxane I.P. once weekly, 30 mg/kg gemcitabine i.p. once weekly or in combination with oseltamivir phosphate at both dosages with Abraxane or gemcitabine. The data in Table 12 show that 2 or 5 mg/kg of oseltamivir phosphate monotherapy efficiently reduced tumour growth in a time-to-progression at day 79 post implantation by 31-35%, but lost its effect by day 93. It is noteworthy that the low dosage of 0.5 mg/kg for Abraxane had little effect on the tumour volume but in combination with 2 or 5 mg/kg of oseltamivir phosphate efficiently reduced tumour growth by 19-25% at day 79 and by 17% at day 84 post implantation when compared to the untreated cohort.

TABLE 12

The effect of co-treatment of oseltamivir phosphate (Tamiflu) and chemotherapeutics on tumour volume (mm$^3$) on PANC-1 human pancreatic cancer cells implanted in RAG1/Cγ double mutant NOD xenograft mice

| Days post Implantation | Treatment (mg/kg) | Tumour volume (mm$^3$) (n mice) | % Inhibition To untreated |
|---|---|---|---|
| 79 | Untreated | 1388 ± 114 (6) | |
| 79 | oseltamivir phosphate (2) | 901 ± 104 (5) | 35% (n.s.) |
| 79 | oseltamivir phosphate (5) | 956 ± 345 (4) | 31% (n.s.) |
| 79 | Abraxane (0.5) | 1655 ± 190 (3) | 0% (n.s.) |
| 79 | Abraxane (0.5) + oseltamivir phosphate (2) | 1130 ± 35 (3) | 19% (n.s.) |
| 79 | Abraxane (0.5) + oseltamivir phosphate (5) | 1041 ± 185 (5) | 25% (n.s.) |
| 79 | Gemcitabine (30) | 200 ± 47 (5) | 86% (p < 0.0001) |
| 79 | Gemictabine (30) + oseltamivir phosphate (2) | 118 ± 38 (6) | 91% (p < 0.0001) |
| 79 | Gemictabine (30) + oseltamivir phosphate (5) | 101 ± 15 (6) | 93% (p < 0.0001) |
| 84 | oseltamivir phosphate (2) | 1079 ± 91 (5) | 22% (n.s.) |
| 84 | oseltamivir phosphate (5) | 1321 ± 503 (4) | 5% (n.s.) |
| 84 | Abraxane (0.5) + oseltamivir phosphate (2) | 1825 ± 615 (2) | 0% (n.s.) |
| 84 | Abraxane (0.5) + oseltamivir phosphate (5) | 1150 ± 167 (5) | 17% (n.s.) |
| 84 | Gemcitabine (30) | 159 ± 52 (5) | 89% (p < 0.0001) |
| 84 | Gemictabine (30) + oseltamivir phosphate (2) | 96 ± 37 (6) | 93% (p < 0.0001) |
| 84 | Gemictabine (30) + oseltamivir phosphate (5) | 118 ± 38 (5) | 91% (p < 0.0001) |
| 93 | oseltamivir phosphate (2) | 1554 ± 469 (2) | 0% (n.s.) |
| 93 | oseltamivir phosphate (5 | 1406 ± 471 (2) | 0% (n.s.) |
| 93 | Gemcitabine (30) | 437 ± 140 (3) | 69% (p < 0.0001) |
| 93 | Gemictabine (30) + oseltamivir phosphate (2) | 167 ± 44 (6) | 89% (p < 0.0001) |
| 93 | Gemictabine (30) + oseltamivir phosphate (5) | 149 ± 29 (5) | 89% (p < 0.0001) |
| 112 | Gemcitabine (30) | 507 ± 357(2) | 63% |
| 112 | Gemcitabine (30) + oseltamivir phosphate (2) | 129 ± 53 (2) | 91% |
| 112 | Gemictabine (30) + oseltamivir phosphate (5) | 306 ± 0 (1) | 78% |

The data in Table 12 also show that gemcitabine monotherapy at 30 mg/kg significantly reduced tumour growth in a time-to-progression at day 79 post implantation by 86%, at day 84 by 89%, at day 93 by 69% and at day 112 by 63%. It is noteworthy that gemcitabine monotherapy began to lose its effect on tumour growth whereby the tumour started to become resistant to the chemotherapeutic actions of gemcitabine but lost its effect by day 93. The combination of gemcitabine with oseltamivir phosphate at the two different dosages significantly reversed the chemotherapeutic resistant of the tumour by maintaining a reduction of 89% at day 93 and 78-91% at day 112 post implantation.

Figure 6:
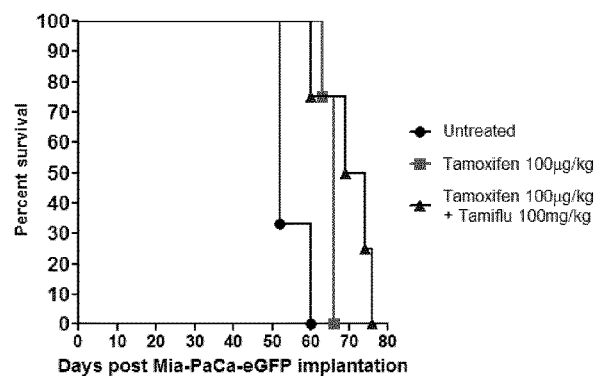
FIG. 6 Survival rates of RAG2/Cγ double mutant mice implanted with MiaPaCa-2-eGFP pancreatic cancer cells following intraperitoneal co-treatment with soluble oseltamivir phosphate daily and tamoxifen. Survival curves are significantly different (p<0.0234) according to log-rank (Mantel-Cox) test.
Figure 7:
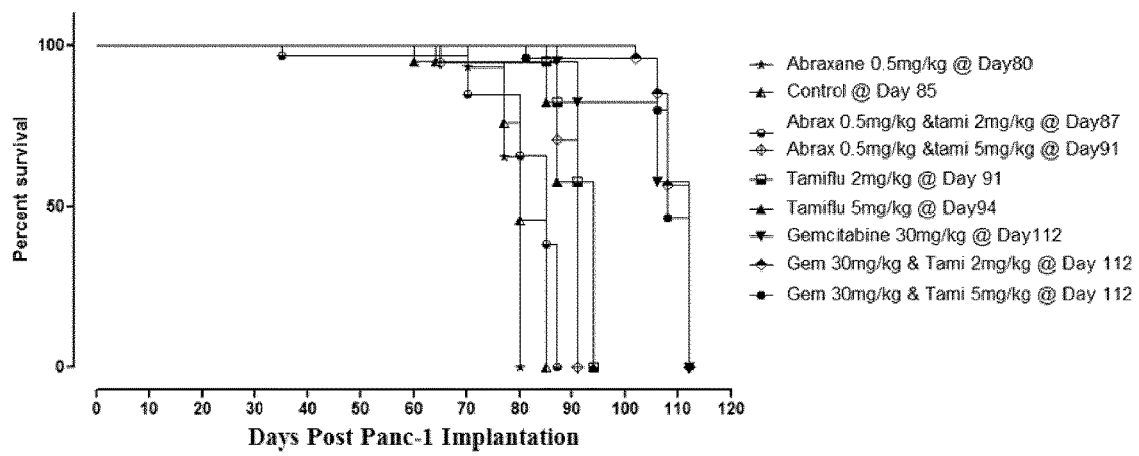
FIG. 7 Survival rates of RAG1/Cγ double mutant NOD mice implanted with PANC-1 human pancreatic cancer cells following intraperitoneal co-treatment with soluble oseltamivir phosphate daily and indicated chemotherapeutics. Survival curves are significantly different according to log-rank (Mantel-Cox) test as follows.

The results shown in FIG. 6 clearly indicate a dramatic significant extension of the survival rates of the tumour bearing mice by 112 days for the combination of gemcitabine and oseltamivir phosphate followed by oseltamivir phosphate monotherapy at days 91 and 94, and Abraxane combination with oseltamivir phosphate at days 87 and 91 compared to the untreated control groups at day 80. The Abraxane monotherapy at the low dosage of 0.5 mg/kg had no effect on the survival rates of the mice compared to the untreated control cohort.

The data in Table 13 indicate the liver metastases as a measure of the average number of nodules and nodule size in mm in each of the above treatment cohorts. There was a significant reduction in liver metastases by greater than 38% in the treated cohorts at different days post implantation when compared to the untreated control cohort. In addition, the combination of gemcitabine with oseltamivir phosphate at 5 mg/kg reduced the liver metastases by 81% compared to the untreated control cohort and further reduced the liver metastases by 10% over the monotherapy of the chemotherapeutic drug at day 109 post implantation.

TABLE 13

The effect of co-treatment of oseltamivir phosphate (Tamiflu)
(10 mg/kg daily) and Alimta (100 mg/kg) or Abraxane (200 mg/kg) on liver
metastases with PANC-1 pancreatic cancer cells implanted in RAG1/Cγ
double mutant NOD xenograft mice

| Days post Implantation | Chemo-drug | Dosage (mg/kg) | Oseltamivir phosphate (mg/kg) | Liver metastases (ave number of nodules) | % Inhibition | Metastases (size, mm) |
|---|---|---|---|---|---|---|
| 79 | untreated | 0 | 0 | 42 | | 0.2-1.2 |
| 90 | | 0 | 2 | 26 | 38% | 0.2-1.3 |
| 90 | | 0 | 5 | 21 | 50% | 0.8-0.2 |
| 78 | abraxane | 0.5 | 0 | 22 | 48% | 0.2-1.0 |
| 78 | abraxane | 0.5 | 2 | 19 | 55% | 0.2-0.7 |
| 90 | abraxane | 0.5 | 5 | 21 | 50% | 0.1-1.0 |
| 101 | gemcitabine | 30 | 0 | 12 | 71% | 0.3-1.5 |
| 110 | gemcitabine | 30 | 2 | 10 | 76% | 0.5-1.2 |
| 109 | gemcitabine | 30 | 5 | 8 | 81% | 0.2-1.5 |

Table 14 includes IC50 data for the inhibition of Neu1 sialidase by analogues of the antiviral agent 2-deoxy-2,3-dehydro-N-acetyneuraminic acid (DANA). Analogues of DANA have been previously disclosed by Magesh et al. [33].

TLR-expressing BMA macrophage cells were grown on 12 mm circular glass slides in culture media containing DMEM supplemented with 10% fetal calf serum. After removing medium, 2.04 mM 4-MUNANA substrate [2'-(4-methylumbelliferyl)-α-D-N-acetylneuraminic acid] (Sigma-Aldrich) in Tris buffered saline pH 7.4 was added to each slide alone (control), with predetermined dose of specific ligand, or in combination of ligand and inhibitor at various doses The substrate is hydrolyzed by sialidase to give free 4-methylumbelliferone which has a fluorescence emission at 450 nm (blue color) following an excitation at 365 nm. Fluorescent images were taken after 2-3 minutes using epi-fluorescent microscopy (Zeiss Imager M2, 40× objective).

This recently developed assay was used to detect sialidase activity on the surface of viable cells. The sialidase activity is revealed in the periphery surrounding the cells using a fluorogenic sialidase specific substrate, 4-MUNANA [2'-(4-methylyumbelliferyl)-α-D-N-acetylneuraminic acid], whose cleavage product 4-methylumbelliferone fluoresces at 450 nm. The inhibitory potency of a series of amide-linked C9 modified DANA (2-deoxy-2,3-dehydro-D-N-acetylneuraminic add) analogues on lipopolysaccharide (LPS)-induced Neu1 sialidase activity was assessed in live BMA macrophage cells. To further elucidate the inhibitory capacity of these DANA analogues, the 50% inhibitory concentration ($IC_{50}$) of each of the compounds was determined by plotting the decrease in sialidase activity against the log of the agent concentration. The results shown in Table 14 suggest that DANA analogues having linear alkyl side chains or 5 or 6-membered cyclic alkyl side chains have increased inhibitory potency on LPS-induced sialidase activity compared to the analogues with branched side chains and to the parent DANA compound. It is believed that the analogues having linear or unbranched side chains may interact with the Neu1 active site more efficiently due to a reduced steric hindrance in this portion of the molecule.

TABLE 14

Inhibitory Activity of analogues of DANA on Neu1 silidase.

| Analogue number | Analogue | $IC_{50}$ (ng/ml) |
|---|---|---|
| B1 | | 4.988 |
| B2 | | 11101 |
| B3 | | 1.56 |

TABLE 14-continued

Inhibitory Activity of analogues of DANA on Neu1 silidase.

| Analogue number | Analogue | IC$_{50}$ (ng/ml) |
|---|---|---|
| B4 | | 989.3 |
| B5 | | 542 |
| B6 | | 29600 |
| B7 | | 246174 |
| B8 | | 408381 |
| B9 | | 400076 |
| B10 | | 153979 |

Based on the results from the in vivo studies to date, the findings signify that oseltamivir phosphate monotherapy or in co-treatment with standard chemotherapeutic drugs prevent the in vivo growth of two different human pancreatic cancers using immunodeficient xenograft mice. The findings provide the proof of principle for an effective oseltamivir phosphate monotherapy or in combination with standard chemotherapeutic drugs for the prevention of (a) human pancreatic tumour growth, and (b) liver metastases. In addition, oseltamivir phosphate monotherapy or in combination with standard clinical chemotherapeutic drugs has promising potential in the treatment of pancreatic cancer, particularly in cases where the tumour has become refractory to conventional chemotherapeutics.

These in vivo data coupled with the in vitro data indicate the effectiveness of oseltamivir phosphate and oseltamivir phosphate in combination with conventional chemotherapeutics provides support for the use of oseltamivir phosphate for the treatment of cancer generally and further for the use of oseltamivir phosphate in combination with known chemotherapeutics for the treatment of cancer.

Furthermore, the in vitro data indicating the effectiveness of analogues of oseltamivir phosphate as potent agents against the tested cancer cells lines indicate that analogues of oseltamivir phosphate may also be used as active agents in the treatment of cancer. It is further noted that the same analogues of oseltamivir phosphate were previously found to be Neu1 sialidase inhibitors. This combination with the in vitro results in the cancer cell assays indicates that these compounds are likely working through the same signalling pathway as oseltamivir phosphate. On this basis a person of skill in the art would understand that further analogues of oseltamivir phosphate having Neu1 sialidase activity would be expected to also be useful for the treatment of cancer.

Additionally it would be understood that other compounds that are Neu1 sialidase inhibitors would also act via the receptor signalling paradigm to affect Trk receptor and EGFR and possibly other receptors and could thereby be used to treat cancer. Examples of such Neu1 sialidase inhibitors are DANA and the analogues of DANA described as B1-B11 above.

While the present invention has been described with reference to specific embodiments and examples, it is to be understood that the invention is not limited to the disclosed examples. To the contrary, the invention is intended to cover various modifications and equivalent arrangements. The invention is further intended to cover the application of various alternatives described in respect of one embodiment with other embodiments where it is suitable to do so. Such modifications and arrangements are included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

The following references are provided as examples of the known art relating to the present invention. The following listing is not intended to comprise a comprehensive list of all relevant art. The entire contents of all references listed in the present specification, including the following documents, are incorporated herein by reference.

References Relating To
1. Hudlicky, T. Processes and Intermediates for the Preparation of Oseltamivir and Analogs Thereof. WO 2009/137916
2. Hudlicky, T.; Wernerm L.; Machara A. Process and Compounds for the Manufacture of Oseltamivir and Analogs thereof, and New Antiviral Agents. WO 2011/047466
3. Jialiang H.; Van den Steen, P. E.; Qing-Xiang S. A.; Ghislain O. Matrix metalloproteinase inhibitors as therapy for inflammatory and vascular diseases. Nature Reviews I Drug Discovery, vol 6, 480-498.
4. Amith, S. R.; Jayanth, P.; Franchuk, S.; Siddiqui, S.; Seyrantepe, V.; Gee, K.; Basta, S.; Beyaert, R.; Pshezhetsky, A. V.; Szewczuk, M. R. Dependence of pathogen molecule-induced toll-like receptor activation and cell function on neu1 sialidase. *Glycoconj J* 2009, 26, 1197-1212.
5. Takahashi, M.; Tsuda, T.; Ikeda, Y.; Honke, K.; Taniguchi, N. Role of n-glycans in growth factor signaling. *Glycoconj J* 2004, 20, 207-212.
6. Amith, S. R.; Jayanth, P.; Franchuk, S.; Finlay, T.; Seyrantepe, V.; Beyaert, R.; Pshezhetsky, A. V.; Szewczuk, M. R. Neu1 desialylation of sialyl alpha-2,3-linked beta-galactosyl residues of toll-like receptor 4 is essential for receptor activation and cellular signaling. *Cell Signal* 2010, 22, 314-324.
7. Woronowicz, A.; Amith, S. R.; De Vusser, K.; Laroy, W.; Contreras, R.; Basta, S.; Szewczuk, M. R. Dependence of neurotrophic factor activation of trk tyrosine kinase receptors on cellular sialidase. *Glycobiology* 2007, 17, 10-24.
8. Hata, K.; Koseki, K.; Yamaguchi, K.; Moriya, S.; Suzuki, Y.; Yingsakmongkon, S.; Hirai, G.; Sodeoka, M.; von Itzstein, M.; Miyagi, T. Limited inhibitory effects of oseltamivir and zanamivir on human sialidases. *Antimicrob Agents Chemother* 2008, 52, 3484-3491.
9. Nan, X.; Carubelli, I.; Stamatos, N. M. Sialidase expression in activated human t lymphocytes influences production of ifn-gamma. *J Leukoc Biol* 2007, 81, 284-296.
10. Shi, D.; Yang, J.; Yang, D.; LeCluyse, E. L.; Black, C.; You, L.; Akhlaghi, F.; Yan, B. Anti-influenza prodrug oseltamivir is activated by carboxylesterase human carboxylesterase 1, and the activation is inhibited by antiplatelet agent clopidogrel. *J Pharmacol Exp Ther* 2006, 319, 1477-1484.
11. Morimoto, K.; Nakakariya, M.; Shirasaka, Y.; Kakinuma, C.; Fujita, T.; Tamai, I.; Ogihara, T. Oseltamivir (tamiflu) efflux transport at the blood-brain barrier via p-glycoprotein. *Drug Metab Dispos* 2008, 36, 6-9.
12. Jayanth, P.; Amith, S. R.; Gee, K.; Szewczuk, M. R. Neu1 sialidase and matrix metalloproteinase-9 cross-talk is essential for neurotrophin activation of trk receptors and cellular signaling. *Cell Signal* 2010, 22, 1193-1205.
13. Amith, S. R.; Jayanth, P.; Franchuk, S.; Siddiqui, S.; Seyrantepe, V.; Gee, K.; Basta, S.; Beyaert, R.; Pshezhetsky, A.; Szewczuk, M. Dependence of pathogen molecule-induced toll-like receptor activation and cell function on neu1 sialidase. *Glycoconjugate Journal* 2009, 26, 1197-1212.
14. Amith, S. R.; Jayanth, P.; Franchuk, S.; Finlay, T.; Seyrantepe, V.; Beyaert, R.; Pshezhetsky, A. V.; Szewczuk, M. R. Neu1 desialylation of sialyl alpha-2,3-linked beta-galactosyl residues of toll-like receptor 4 is essential for receptor activation and cellular signaling. *Cell Signal* 2010, 22 314-324.
15. Miyagi, T.; Sagawa, J.; Konno, K.; Tsuiki, S. Immunological discrimination of intralysosomal, cytosolic, and two membrane sialidases present in rat tissues. *J. Biochem. (Tokyo)* 1990, 107, 794-798.
16. Rodriguez, J. A.; Piddini, E.; Hasegawa, T.; Miyagi, T.; Dotti, C. G. Plasma membrane ganglioside sialidase regulates axonal growth and regeneration in hippocampal neurons in culture. *J. Neurosci.* 2001, 21, 8387-8395.
17. Sasaki, A.; Hata, K.; Suzuki, S.; Sawada, M.; Wada, T.; Yamaguchi, K.; Obinata, M.; Tateno, H.; Suzuki, H.; Miyagi, T. Overexpression of plasma membrane-associated sialidase attenuates insulin signaling in transgenic mice. *J. Biol. Chem.* 2003, 278, 27896-27902.
18. Papini, N.; Anastasia, L.; Tringali, C.; Croci, G.; Bresciani, R.; Yamaguchi, K.; Miyagi, T.; Preti, A.; Prinetti, A.; Prioni, S.; Sonnino, S.; Tettamanti, G.; Venerando, B.; Monti, E. The plasma membrane-associated sialidase mmneu3 modifies the ganglioside pattern of adjacent cells supporting its involvement in cell-to-cell interactions. *J. Biol. Chem.* 2004, 279, 16989-16995.
19. Yamaguchi, K.; Hata, K.; Koseki, K.; Shiozaki, K.; Akita, H.; Wada, T.; Moriya, S.; Miyagi, T. Evidence for mitochondrial localization of a novel human sialidase (neu4). *Biochem. J.* 2005, 390, 85-93.
20. Seyrantepe, V.; Poupetova, H.; Froissart, R.; Zabot, M. T.; Maire, I.; Pshezhetsky, A. V. Molecular pathology of neu1 gene in sialidosis. *Hum. Mutat.* 2003, 22, 343-352.

21. Lukong, K. E.; Elsliger, M. A.; Chang, Y.; Richard, C.; Thomas, G.; Carey, W.; Tylki-Szymanska, A.; Czartoryska, B.; Buchholz, T.; Criado, G. R.; Palmeri, S.; Pshezhetsky, A. V. Characterization of the sialidase molecular defects in sialidosis patients suggests the structural organization of the lysosomal multienzyme complex. *Hum. Mol. Genet.* 2000, 9, 1075-1085.
22. Hinek, A.; Pshezhetsky, A. V.; Von, I. M.; Starcher, B. Lysosomal sialidase (neuraminidase-1) is targeted to the cell surface in a multiprotein complex that facilitates elastic fiber assembly. *J. Biol. Chem.* 2006, 281, 3698-3710.
23. Liu, D.; Zhang, Y.; Dang, C.; Ma, Q.; Lee, W.; Chen, W. Sirna directed against trka sensitizes human pancreatic cancer cells to apoptosis induced by gemcitabine through an inactivation of pi3k/akt-dependent pathway. *Oncol Rep* 2007, 18, 673-677.
24. Yogalingam, G.; Bonten, E. J.; van de Vlekkert, D.; Hu, H.; Moshiach, S.; Connell, S. A.; d'Azzo, A. Neuraminidase 1 is a negative regulator of lysosomal exocytosis. *Dev Cell* 2008, 15, 74-86.
25. Seyrantepe, V.; Iannello, A.; Liang, F.; Kanshin, E.; Jayanth, P.; Samarani, S.; Szewczuk, M. R.; Ahmad, A.; Pshezhetsky, A. V. Regulation of phagocytosis in macrophages by neuraminidase 1. *Journal of Biological Chemistry* 2010, 285, 206-215.
26. Chen, X. P.; Enioutina, E. Y.; Daynes, R. A. The control of il-4 gene expression in activated murine t lymphocytes: A novel role for neu-1 sialidase. *J Immunol* 1997, 158, 3070-3080.
27. Uberall, I.; Kolar, Z.; Trojanec, R.; Berkovcova, J.; Hajduch, M. The status and role of erbb receptors in human cancer. *Exp Mol Pathol* 2008, 84, 79-89.
28. Li, D.; Ji, H.; Zaghlul, S.; McNamara, K.; Liang, M. C.; Shimamura, T.; Kubo, S.; Takahashi, M.; Chirieac, L. R.; Padera, R. F.; Scott, A. M.; Jungbluth, A. A.; Cavenee, W. K.; Old, L. J.; Demetri, G. D.; Wong, K. K. Therapeutic anti-egfr antibody 806 generates responses in murine de novo egfr mutant-dependent lung carcinomas. *J Clin Invest* 2007, 117, 346-352.
29. Takahashi, M.; Yokoe, S.; Asahi, M.; Lee, S. H.; Li, W.; Osumi, D.; Miyoshi, E.; Taniguchi, N. N-glycan of erbb family plays a crucial role in dimer formation and tumor promotion. *Biochim Biophys Acta* 2008, 1780, 520-524.
30. Zwick, E.; Bange, J.; Ullrich, A. Receptor tyrosine kinases as targets for anticancer drugs. *Trends Mol Med* 2002, 8, 17-23.
31. Arabkhari, M.; Bunda, S.; Wang, Y.; Wang, A.; Pshezhetsky, A. V.; Hinek, A. Desialylation of insulin receptors and igf-1 receptors by neuraminidase-1 controls the net proliferative response of 16 myoblasts to insulin. *Glycobiology* 2010, 20, 603-616.
32. Gilmour, A. M.; Jayanth, P.; Szewczuk, M. R. Ligand-Induced EGFR Activation is dependent on Neu1 Sialidase and MMP-9 Cross-Talk poster presentation—2010 Annual Conference of the Society for Glycobiology, Nov. 7-10, 2010, St. Petersburg Beach, Fla.
33 Magesh, S. et al. Design, Synthesis and Biological Evaluation of Human Sialidase Inhibitors, *Biorganic and Medicinal Chemistry Letters* 2008, (18), 532-537.

What is claimed is:

1. A method for the treatment of cancer comprising administering to a subject in need thereof a pharmaceutically effective amount of oseltamivir phosphate, wherein the cancer is pancreatic cancer, breast cancer, ovarian cancer or prostate cancer.

2. The method of claim 1 wherein the cancer is pancreatic cancer, breast cancer or ovarian cancer.

3. The method of claim 2 wherein the cancer is pancreatic cancer.

4. The method of claim 1 wherein the cancer is refractory to standard treatment.

5. The method of claim 1 wherein the cancer is metastatic cancer.

6. A method for the treatment of cancer, wherein the cancer is pancreatic cancer, breast cancer, ovarian cancer or prostate cancer, comprising:
   administering to a subject in need thereof an therapeutically effective amount of
   (a) oseltamivir phosphate; and
   (b) one or more chemotherapeutic agents;
   wherein (a) and (b) are performed concurrently or sequentially in any order.

7. The method of claim 6 wherein the chemotherapeutic agent is cisplatin, cis platinum, cis-diamminedichloroplatinum(II), fluorouracil, gemcitabine, tamoxifen, pemetrexed or protein-bound paclitaxel (ABRAXANE).

8. The method of claim 6 wherein the cancer is refractory to standard treatment.

9. The method of claim 6 wherein the cancer is metastatic cancer.

10. A method for the treatment of metastasis of cancer, comprising administering to a patient in need thereof a pharmaceutically effective amount of oseltamivir phosphate, wherein the cancer is selected from the group consisting of pancreatic cancer, breast cancer, ovarian cancer or prostate cancer.

11. A method for the treatment of cancer comprising administering to a subject in need thereof a pharmaceutically effective amount of a Neu1 sialidase inhibitor, wherein the cancer is pancreatic cancer, breast cancer, ovarian cancer or prostate cancer, wherein the Neu1 sialidase inhibitor is oseltamivir phosphate.

12. The method of claim 11 wherein the Neu1 sialidase inhibitor acts through a receptor signalling pathway to inhibit one or more growth receptors implicated in cancer.

13. The method of claim 12 wherein the one or more growth receptor is EGFR, insulin-like receptor, VEGF, Toll-like receptor, Trk A receptor or Trk B receptor.

14. A method for the prevention of metastasis of cancer, comprising administering to a patient in need thereof a pharmaceutically effective amount of oseltamivir phosphate, wherein the cancer is selected from the group consisting of pancreatic cancer, breast cancer, ovarian cancer or prostate cancer.

15. A pharmaceutical composition comprising oseltamivir phosphate in a formulation in a pharmaceutically effective amount for the treatment of cancer and a chemotherapeutic agent, wherein the cancer is pancreatic cancer, breast cancer, ovarian cancer or prostate cancer, wherein the composition is suitable for injection, and the chemotherapeutic agent is cisplatin, fluorouracil, tamoxifen, gemcitabine, or abraxane.

16. A kit comprising oseltamivir phosphate in a pharmaceutically effective amount for the treatment of cancer, one or more chemotherapeutic agents and instructions for use in the treatment of cancer, wherein the cancer is pancreatic cancer, breast cancer, ovarian cancer or prostate cancer, and the chemotherapeutic agent is cisplatin, fluorouracil, tamoxifen, gemcitabine, or abraxane.

* * * * *